US011365224B2

(12) United States Patent
Zhong et al.

(10) Patent No.: US 11,365,224 B2
(45) Date of Patent: Jun. 21, 2022

(54) PROGRAMMABLE AND PRINTABLE BIOFILMS AS ENGINEERED LIVING MATERIALS

(71) Applicant: ShanghaiTech University, Shanghai (CN)

(72) Inventors: Chao Zhong, Shanghai (CN); Jiaofang Huang, Shanghai (CN); Suying Liu, Shanghai (CN); Chen Zhang, Shanghai (CA)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 17/169,504

(22) Filed: Feb. 7, 2021

(65) Prior Publication Data

US 2021/0198325 A1 Jul. 1, 2021

Related U.S. Application Data

(63) Continuation of application No. PCT/CN2019/100160, filed on Aug. 12, 2019.

(30) Foreign Application Priority Data

Aug. 14, 2018 (WO) ................ PCT/CN2018/100538

(51) Int. Cl.

| | |
|---|---|
| ***C12N 1/00*** | (2006.01) |
| ***C07K 14/00*** | (2006.01) |
| ***C07K 14/32*** | (2006.01) |
| ***C12N 11/10*** | (2006.01) |

(52) U.S. Cl.
CPC .............. *C07K 14/32* (2013.01); *C12N 11/10* (2013.01); *C07K 2319/21* (2013.01)

(58) Field of Classification Search
CPC ................ A01N 63/22; C07K 2319/00; C07K 2319/21; C12N 15/75; C12N 1/20; C12N 15/62; C12Y 302/01004
USPC ............................................. 435/69.7, 252.3
See application file for complete search history.

(56) References Cited

PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Abraham Bairi, Intl. Commun. Heat & Mass Transf., 2021, 126, pp. 1-8.*

* cited by examiner

*Primary Examiner* — Robert B Mondesi
*Assistant Examiner* — Mohammad Y Meah
(74) *Attorney, Agent, or Firm* — Richard Aron Osman

(57) ABSTRACT

Three-dimensional, living, self-regenerative structures of predetermined geometry comprising solidified print material comprising a biofilm of *Bacillus subtilis* comprise a TasA-R protein, wherein R is a recombinant, heterologous functional group, wherein the TasA-R provides a preferably tunable physiochemical property like viscosity, reactivity, affinity as a function of the R group.

20 Claims, 3 Drawing Sheets

Specification includes a Sequence Listing.

Fig. 1A
Fig. 1B
Fig. 1C
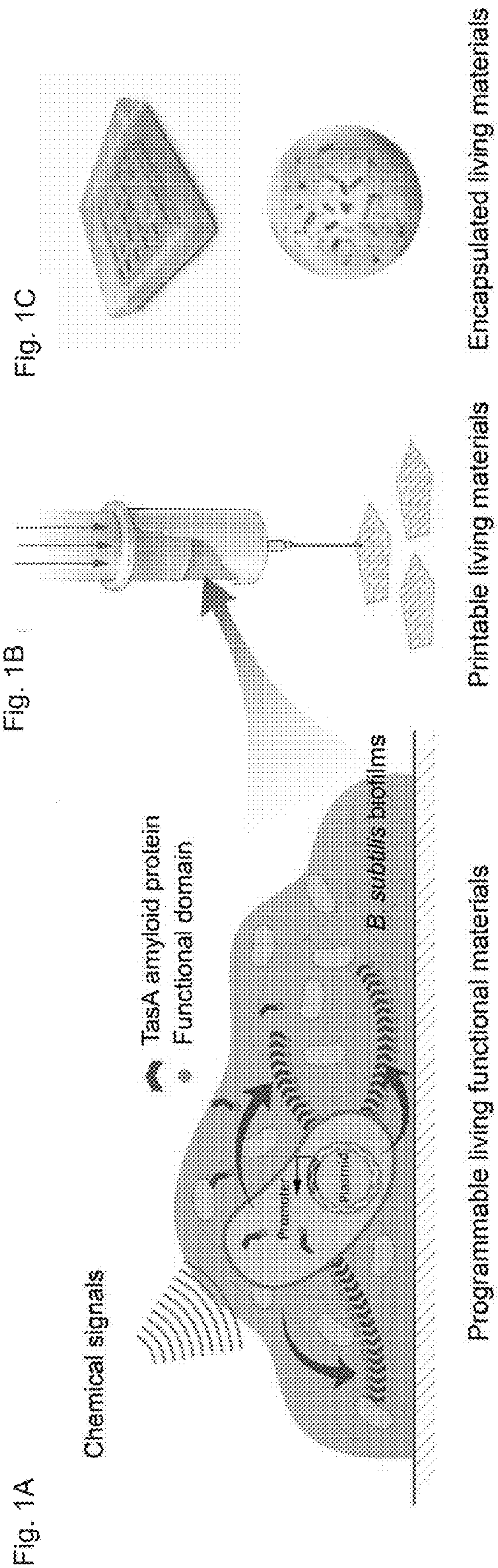
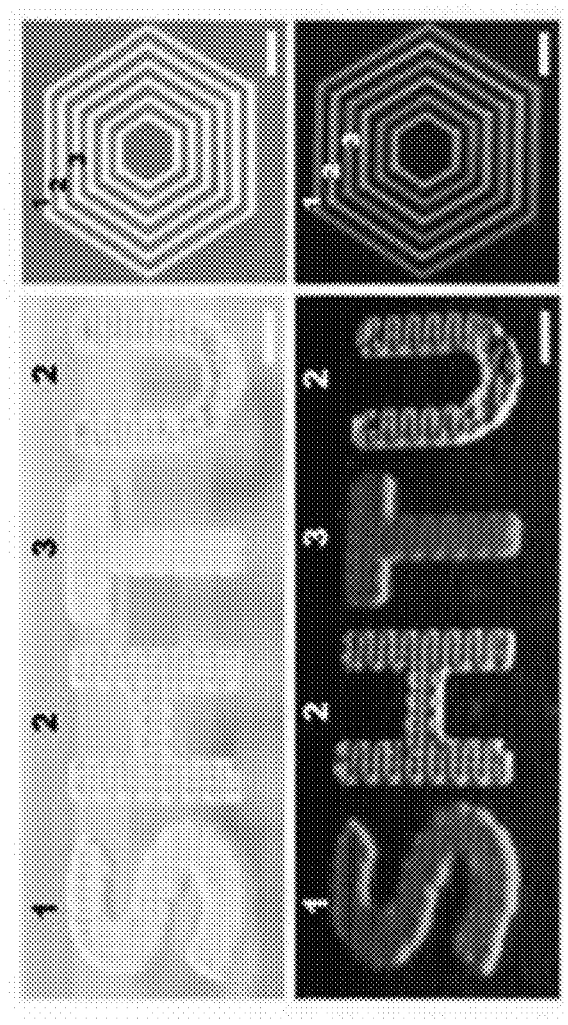
Fig. 2

Biofilms
3D printing on glass
Transfer
Upside down
Self-regeneration on agar plate As-printed
1st
2nd G'
G"
As-grown
1st
2nd
G', G" (Pa)
10000
1000
100
10
1
2
3
Self-generated biofilms Brightfield
Fluorescence Brightfield
Fluorescence

PROGRAMMABLE AND PRINTABLE BIOFILMS AS ENGINEERED LIVING MATERIALS

INTRODUCTION

Bacterial biofilms, skeletal tissue, and other natural biological systems are multifunctional and environmentally responsive assemblages of living and non-living components[1]. As these natural systems grow, self-repair, and adapt to the environment, they have distinctive "living" attributes that are beyond the reach of the vast majority of existing synthetic materials[2]. Scientists and engineers have long envisioned harnessing these attributes to create dynamic, environmentally responsive, and tunable "living functional materials" that incorporate both non-living components and living cells[3,4].

Biofilms are formed by bacteria on various surfaces via the synthesis and secretion of a cohesive and protective extracellular matrix that helps them tolerate harsh or low nutrition environments[5]. Scaffolds for bacterial biofilm formation often consist of amyloid fibers—proteins that self-assemble to form various cross-beta nano-architectures[6,7]. These amyloid fibers are known to function in a number of physiological processes required for bacterial growth and survival, including adhesion to diverse interfaces and/or host tissues[8], detoxification of toxic compounds[9], resistance to antibiotics[10], morphological differentiation of filamentous bacteria[11], and electron transport[12]. Recent bioengineering work has exploited amyloid fibers to develop both engineered cellular consortia and artificial biofilms[1, 13-15]. For example recent work has demonstrated the controllable and autonomous patterning of curli fibrils assembled in *Escherichia coli* cells' and a biofilm-integrated nanofiber display (BIND) system; with this system the *E. coli* biofilm extracellular matrix can be programmed via manipulation of genetically engineered functional peptide domains of the CsgA protein[15].

Despite these important advances, multiple technical challenges must be overcome before amyloid fibers can be used routinely and reliably in the design of living functional materials. In engineered biofilms research, known problems include the inability of bacterial export machinery to secret large proteins (for example, *E. coli* curli system is limited to secret short peptides or protein domains containing 59 amino acids)[15], which thereby reduces the scope of possible material functionalities, as well as difficulties with the controlled processing of such complex materials into customizable three-dimensional (3D) structures with well-defined designed geometries[6]. Furthermore, considering that these materials are living and given the potential risks that live bacteria present to human beings and the environment[16], it is now appreciated that in addition to using bacterial species that are considered safe, the careful packaging of such materials into confined environments is a particularly important and necessary element of their design. Thus, perhaps it is unsurprising that the bio-manufacture of programmable engineered biofilms remains a sparsely explored area of research.

SUMMARY OF THE INVENTION

Bacterial biofilms can be programmed to produce living materials with self-healing and evolvable functionalities. However, the wider use of artificial biofilms has been hindered by limitations in processability and functional protein secretion capacity. We describe a highly flexible and tunable living functional materials platform based on the TasA amyloid machinery of the bacterium *Bacillus subtilis*. We demonstrate that genetically programmable TasA fusion proteins harboring diverse functional proteins or domains can be secreted and can assemble into diverse extracellular nano-architectures with tunable physiochemical properties. Our engineered biofilms have the viscoelastic behaviors of hydrogels and can be precisely fabricated into microstructures having a diversity of three-dimensional (3D) shapes using 3D printing and microencapsulation techniques. Notably, these long-lasting and environmentally responsive fabricated living materials remain alive, self-regenerative, and functional. This new tunable platform offers previously unattainable properties for a variety of living functional materials having applications in biomaterials, biotechnology, and biomedicine.

The invention provides methods and compositions for producing programmable and printable biofilms as engineered living materials. In an aspect the invention provides a three-dimensional, living, self-regenerative structure of predetermined geometry comprising solidified print material comprising a biofilm of *Bacillus subtilis* comprising a TasA-R protein, wherein R is a recombinant, heterologous functional group, wherein the TasA-R provides a preferably tunable physiochemical property like viscosity, reactivity, affinity as a function of the R group.

In embodiments:

the R group comprises a His-tag, and the TasA-R protein is optionally complexed with a gold nanoparticle;

the geometry is at a resolution of resolution of 50-250 um, preferably 100-200 um; and/or the structure is encapsulated in hydrogel or microgel In another aspect the invention provides a method of making the disclosed structures comprising printing the structure.

In another aspect the invention the invention provides a method of replicating the disclosed structures comprising contacting the structure with a matrix comprising a growth medium wherein the *Bacillus subtilis* of the structure grow to form a replicant structure.

The invention includes all combinations of recited particular embodiments as if each combination had been laboriously recited.

BRIEF DESCRIPTION OF THE DRAWINGS

FIGS. 1A-1C. Design for a programmable and printable *B. subtilis* biofilm production platform. (FIG. 1A) Schematic of the programmable living biofilm platform based on the TasA amyloid export machinery of *B. subtilis*; (FIG. 1B) Schematic of a printable living biofilm using a 3D printing technique. The living *B. subtilis* biofilms exhibit viscoelastic properties that make them suitable for 3D printing; (FIG. 1C) Schematic showing that the living *B. subtilis* biofilms maintain their natural viability and various cellular capacities such as self-regeneration when trapped in hydrogels or microcapsules.

FIG. 2. 3D complex printing of TasA-HisTag biofilms and inorganic NPs into diverse patterns. Digital photographs of the printed complex structures taken under normal (top) and UV light (bottom). Numbers 1, 2, and 3 refer to the TasA-HisTag biofilms with the following types of immobilized quantum dots (QDs): (1) blue CdZnS@ZnS QDs, (2) green CdZnSeS@ZnS QDs, and (3) red Co-NTA CdSeS@ZnS QDs, with maximum emission peak wavelengths at 464, 496, and 627 nm, respectively. Scale bars: 5 mm.

(FIG. 3A) 3D printing of engineered *B. subtilis* biofilms into patterned structures on glass slides and self-regeneration of patterned biofilms on agar plates for two continuous generations: cartoon showing the 3D printing and self-regeneration processes. (FIG. 3B) For the self-regeneration experiments, the 3D printed samples were placed upside down on an agar plate. From left to right: the printed patterns on glass slide, the biofilms re-growing in the hexagonal patterns on the first nutrient-rich agar plate, and the biofilm still growing in the initial hexagonal patterns on the second nutrient-rich agar plate (right). (FIG. 3C) Comparison of the storage modulus (G') and the loss modulus (G") of the initially grown and self-regenerated biofilms. (FIGS. 3D-3E) Functional performance of the bio-fabricated biofilms: (FIG. 3D) trapped inside a mixed hydrogel containing 5% w/v gelatin and 2% w/v sodium alginate or (FIG. 3E) microencapsulated inside alginate-poly-(L-lysine)-alginate (APA) microcapsules. When immersed into a solution containing IPTG, in both cases the trapped biofilms emitted red fluorescence throughout a 5-day culture period (middle panel). The encapsulation of biofilms in alginate hydrogel microspheres was based on a microencapsulation technique[34]. Fluorescence images were acquired with the 587 nm channel. Scale bars: 5 mm in b, 1 mm in d, and 100 μm in e. Measurements are the average of triplicate cultures with s.e.m. displayed.

DESCRIPTION OF PARTICULAR EMBODIMENTS OF THE INVENTION

Figures 3A, 3B, 3C, 3D, 3E:
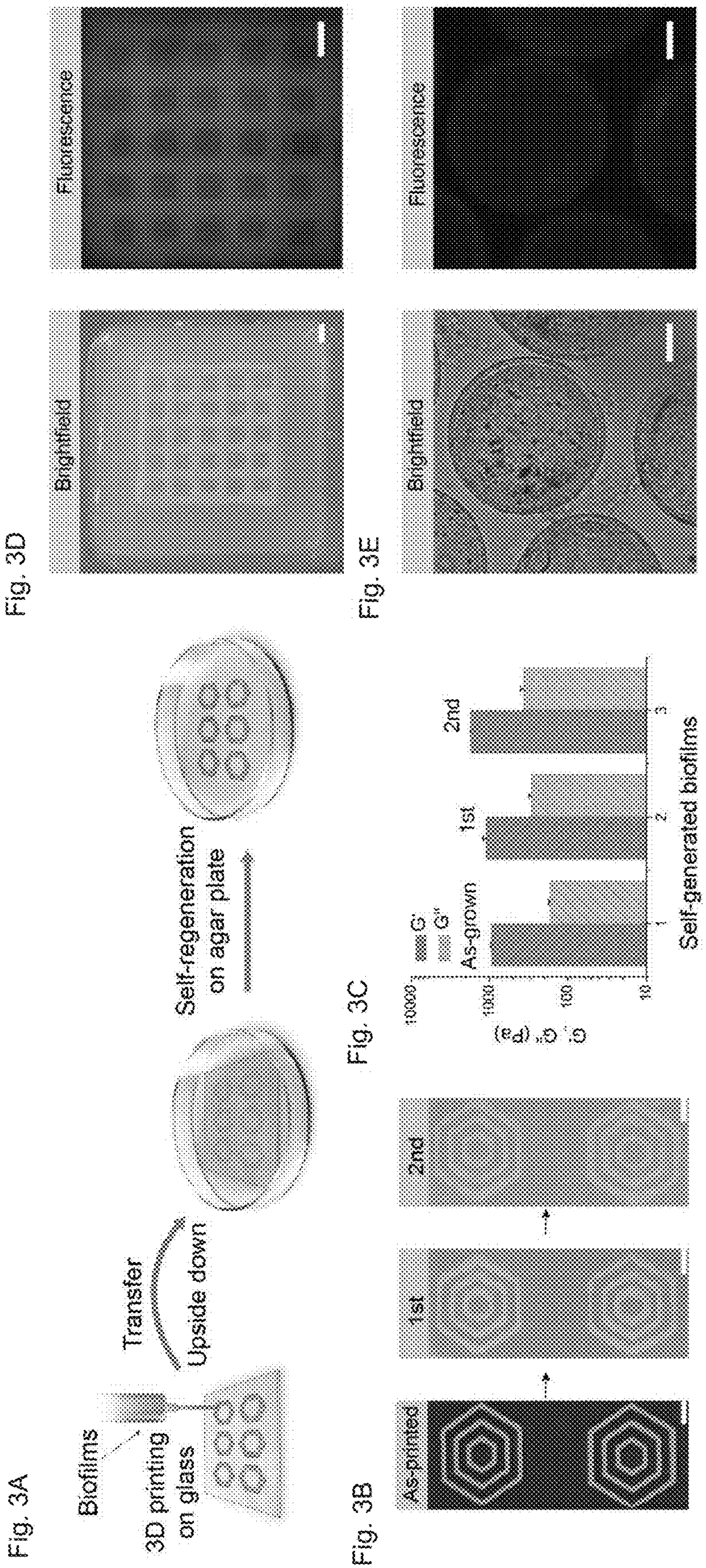
FIGS. 3A-3E. Self-regeneration, bio-fabrication, long-term viability, and functional performance of hydrogel-trapped *B. subtilis* biofilms using 3D printing and microencapsulation techniques.
Figures 4A, 4B, 4C, 4D, 4E, 4F, 4G:
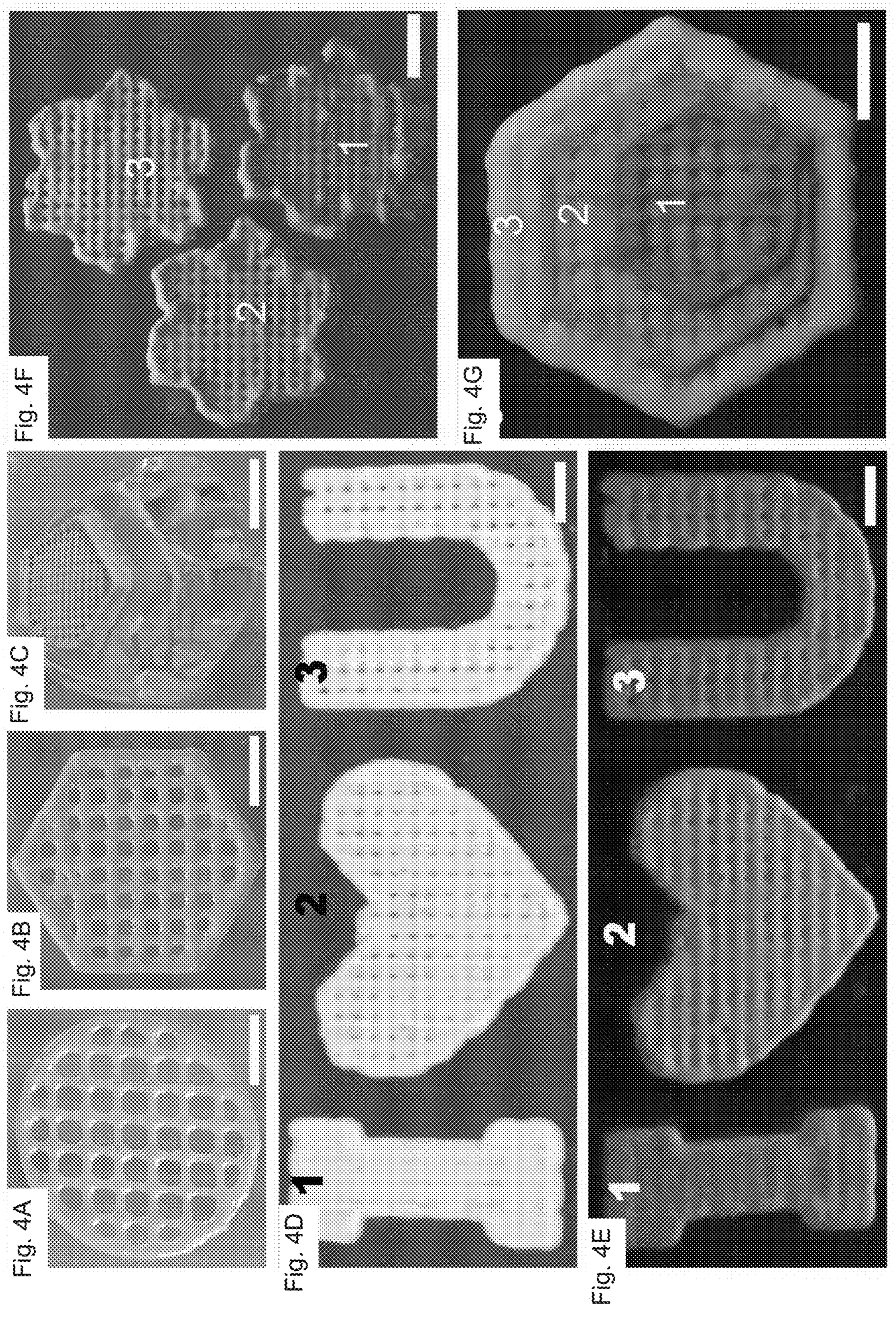
FIGS. 4A-4G. Printed biofilms and complex biofilms/QDs structures through 3D printing technique. Digital camera images showing biofilms printed on the (FIG. 4A) glass, (FIG. 4B) PV plate, and (FIG. 4C) gelatin hydrogel. Digital camera images showing printed complex biofilms/QD structures under (FIG. 4D) normal and (FIGS. 4E-4G) 350 nm UV light. Numbers 1, 2, and 3 in d-g refer to the TasA-HisTag biofilms with the following types of immobilized quantum dots (QDs): (1) blue CdZnS@ZnS QDs, (2) green CdZnSeS@ZnS QDs, and (3) red Co-NTA CdSeS@ZnS QDs, with maximum emission peak wavelengths at 464 nm, 496 nm, and 627 nm, respectively. Scale bars: 5 mm.

The embodiments and examples herein are provided by way of illustration only and not by way of limitation. Those skilled in the art will readily recognize a variety of noncritical parameters that could be changed or modified to yield essentially similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Design for a Programmable *B. subtilis* Biofilm Production Platform

We used a combination of genetic engineering and bio-manufacturing approaches to manipulate biofilms produced by *Bacillus subtilis*, a Gram-positive aerobic endospore-forming bacterium that is "generally regarded as safe" (GRAS). We developed a highly flexible and tunable living functional materials platform with several practical applications (FIGS. 1A-1C). Specifically, we harnessed the TasA amyloid machinery of *B. subtilis* and developed genetically programmable TasA fusion proteins with diverse domain combinations offering versatile functionality for cell biology, enzymology, and other applications. These fusion proteins can be secreted and can self-assemble around living cells into diverse extracellular nano-architectures with tunable physiochemical properties (e.g., viscoelasticity) (FIG. 1A) and can also be flexibly configured in space (e.g., 3D printing of living biofilms) (FIG. 1B). In the presence of chemical inducers, *B. subtilis* cells express rationally designed TasA fusion proteins comprising the amyloidogenic TasA domain (blue) and a tunable functional domain (green). Upon secretion, the fusion proteins self-assemble into extracellular fibrous networks that are closely associated with cell surfaces, resulting in programmable biofilms with tunable non-natural functional properties. Importantly, while retaining their natural viability and various cellular capacities like self-regeneration, these constructed living materials can also be designed to exhibit non-natural functionalities that are dependent on the incorporated functional domains, including altered enzymatic activity, red fluorescence, and the capacity for templated assembly of inorganic nanoparticles (NPs).

In a series of increasingly complex proof-of-concept demonstrations, we deployed these engineered biofilms in fluorescence detection, conjugation chemistry, single substrate bioremediation, and multi-reaction bioremediation cascades incorporating NPs. We also exploited the intrinsic viscoelastic properties of our engineered biofilms and fabricated well-defined "living shapes" and then trapped these materials into hydrogels and microgels using 3D printing and microencapsulation techniques (FIG. 1C). Finally, as these bacterial biofilms are composed of living cells in well-defined geometries, we evaluated their self-regeneration capacity, storage, and long-term viability. Our study demonstrates that we have constructed a programmable and printable living functional material platform that provides applications in nano-manufacturing, biocatalysis, biomedicine, and other technical fields.

Unlike *E. coli* or other Gram-negative bacteria, *B. subtilis* has only one outer membrane, a feature that has long made this bacterium popular for the production of secreted enzymes and other proteins at an industrial scale[17]. Unlike the adherent *E. coli* cells that form biofilms at various interfaces, *B. subtilis* biofilms tend to form at air-water interfaces and exhibit viscoelastic properties that are attractive for fabrication applications[18-20]. The production of amyloid fibers in *B. subtilis* biofilms is tightly regulated by the tapA-sipW-tasA gene operon, which encodes TasA and TapA as, respectively, major and minor amyloid components of biofilms. TapA protein acts as molecular nucleators for the extracellular assembly of TasA protein into nanofibers on the cell surface, providing structural integrity to *B. subtilis* biofilms[21]. Notably, TasA protein differs from other biofilm-forming amyloid proteins by the apparent lack of repeats in its sequence[22].

We focused our engineering efforts on TasA, because this amyloid family protein is well known for having high tolerance to chemical elaboration and functionalization without disruption of its self-assembly capacity[23, 24]. To assess whether genetically modified TasA can be secreted and can self-assemble into extracellular nanofibers, we first established a platform for the inducible transcriptional and translational control over the expression of variously functionalized genetically engineered TasA variants. We used IPTG-inducible expression plasmids to express the engineered variants ("TasA-R") and used these plasmids to transform a *B. subtilis* strain that we had constructed (2569 ΔtasAΔsinRΔeps). We designed this strain to facilitate the detection of functionalized TasA-R variants, to lack the sinR gene that is known to limit biofilm production by repressing the eps and tasA operons, and to lack the epsA~O gene cluster, which encodes exopolysaccharides (EPS).

Consistent with our design, the biofilm-defective strain *B. subtilis* 2569 ΔtasAΔsinRΔeps (ΔtasAΔsinRΔeps) did not produce extracellular TasA fibers, but upon IPTG induction the ΔtasAΔsinRΔeps cells harboring the exogenous expression plasmid pHT01 for the TasA-R variants (e.g., TasA-mCherry) restored amyloid fiber production. Amyloid production was confirmed by transmission electron microscopy (TEM), which showed that immuno-gold labeled anti-TasA antibodies could specifically bind to the TasA-R fibrous networks. Biofilm production was further confirmed with a standard crystal-violet (CV) assay, in which the presence of IPTG increased the biomass for each of the TasA-R variants compared to their controls without IPTG induction. In addition, we also compared the morphologies and diameters of the differently functionalized nanofibers (TasA-HisTag, TasA-mefp5, and TasA-OPH as representatives) based on TEM imaging and found that there was an obvious trend in the diameters of the different types of nanofibers: the diameter of the nanofibers increased as the size of the monomer fusion domains increased; order: TasA-OPH (18.7±2.3 nm)>TasA-mefp5 (15.7±2.0 nm)>TasA-HisTag (13.6±1.6 nm).

Functional Characterization of the Engineered Functions of *B. subtilis* Biofilms We next assessed whether the biofilms containing the secreted TasA-R nanofibers had new functional properties as a result of their various engineered fusion domains.

| Type | Peptide | Length | Specific Functions | Ref |
|---|---|---|---|---|
| Short peptide | HisTag | 6 | Affinity Tag | 42 |
| | SpyTag | 13 | Covalent binding | 25 |
| Protein domain | Mefp3 | 48 | Mussel adhesive protein | 43 |
| | Mms6 | 59 | Magnetite templating | 44 |
| | Mefp5 | 74 | Mussel adhesive protein | 43 |
| Fluor. Protein | Maple | 237 | Fluorescent protein | 45 |
| | mCherry | 237 | Fluorescent protein | 46 |
| Enzyme | PETase | 290 | PET degradation enzyme | 26 |
| | OPH | 337 | Organic phophohydrolase | 47 |
| | MHETase | 603 | MHET degradation enzyme | 26 |

We started with the TasA-R variants fused to the mCherry protein (TasA-mCherry) and found that, upon IPTG induction, biofilms expressing TasA-mCherry nanofibers exhibited red fluorescence, validating that mCherry retains its function when expressed in a biofilm generated by our platform. We next generated TasA-R variants that use the covalent isopeptide bond formation reaction between the SpyTag (TasA-SpyTag) and SpyCatcher protein binding partners[25] as a fusion with the fluorescent protein GFP as a readout (SpyCatcher-GFP). We observed green fluorescence only when we added free SpyCatcher-GFP protein to biofilms containing TasA-SpyTag nanofibers (but not with TasA-HisTag nanofibers or other control), demonstrating that the observed fluorescence in TasA-SpyTag nanofibers was sample specific and the fused SpyTag indeed remained functional in the form of TasA-SpyTag nanofibers.

To further explore the capacities of our programmable biofilm platform, we engineered a strain producing extracellular TasA-MHETase nanofibers. MHETase—an enzyme that degrades the toxic industrial compound MHET (mono (2-hydroxyethyl) terephthalic acid) into the less toxic TPA (terephthalic acid)—was purposely chosen here as a test not only for its practical use but also because it is quite large (603 amino acids)[26]. Upon IPTG induction, the cells produced and assembled TasA-MHETase nanofibers on their surfaces. We next treated these IPTG-induced biofilms with free MHET and used HPLC-MS to detect TPA. Our results confirmed that the TasA-MHETase nanofibers retained their MHETase enzymatic activity. The relationship between catalytic rate and substrate concentration in the TasA-MHETase biofilm system followed typical Michaelis-Menten kinetics. It is notable that although engineered *E. coli* biofilms with single enzymatic capacities have been reported, such examples required the use of covalent reactions between displayed SpyTags on biofilms and separately purified SpyCatcher-enzyme fusions[27], a multistep process that involves considerably more labor than our single-step IPTG induction of *B. subtilis* TasA-MHETase biofilms.

Having demonstrated a single enzyme application, we next tested whether our programmable biofilm platform could be used for multistep reactions (i.e., biocatalytic cascades) to degrade organophosphate pesticides into harmless chemicals. We chose a two-step cascade consisting of 1) the organophosphate hydrolase (OPH)-catalyzed degradation of the pesticide paraoxon (PAR) into the less harmful intermediate product paranitrophenol (PNP), and 2) a reaction catalyzed by HisTag-immobilized gold NPs (AuNPs) in which PNP is further degraded into harmless p-aminophenol (PAP). The TasA-HisTag nanofibers use His-metal-coordination chemistry to promote the assembly of AuNPs.

We therefore engineered two separate strains that respectively expressed and assembled functional TasA-OPH and TasA-HisTag nanofibers. We first confirmed that a biofilm containing only TasA-OPH nanofibers could efficiently catalyze the PAR-to-PNP reaction and that a biofilm containing only the TasA-HisTag nanofibers with the presence of AuNPs and $NaBH_4$ could efficiently catalyze the PNP-to-PAP reaction. While this PNP degradation generally followed first-order reaction kinetics, it was interesting to note that the TasA-HisTag-immobilized NPs actually outperformed free NPs (control reaction in aqueous solution) for the degradation of PNP. This surprising finding can perhaps be ascribed to enhanced absorption of PAR onto the biofilm. We next co-cultured the strains to produce a single, hybrid biofilm that contained both the TasA-OPH nanofibers (enzyme-mediated degradation) and the TasA-HisTag nanofibers (NP-mediated degradation). With both AuNPs and $NaBH_4$ present, each of the two degradation reactions of the cascade exhibited kinetics similar to those of the separate reactions for the single-strain biofilms.

The complex and heterogeneous features of the fibrous networks in the biofilm of this co-cultured hybrid reaction system were assessed with TEM imaging, which confirmed that AuNPs specifically bound to TasA-HisTag nanofibers rather than to TasA-OPH nanofibers. The immobilized AuNPs on the nanofibers circumvent direct contact of NPs with bacteria, preventing potential damage to the cells caused by free NPs[28]. Thus, our programmable *B. subtilis* biofilm platform can be used to make hybrid catalytic systems coupling living biofilms with inorganic NPs. The ability to grow biofilms comprising multiple strains and to use hybrid reaction systems in designs that merge the various advantages of each component demonstrates that our methods can produce complex and multi-component biofilms as eco-friendly, high-efficiency, and self-regenerating catalytic systems for a very wide range of applications.

Viscoelastic Properties and Biofabrication of Living Functional Materials

Having demonstrated that our platform can be used to make multi-strain biofilms capable of complex multistep chemistries, we next explored whether we could finely manipulate biofilm geometries. The ability to precisely control the physical context for complex chemical reactions would have obvious utility in nano-manufacturing and materials applications[20, 29, 39]. Wild-type *B. subtilis* biofilms are known to form complex gel-like materials at water-air interfaces and on solid agar plates with viscoelastic properties that in theory would be attractive for many biofabrication applications like printing. We therefore characterized the viscoelastic properties of wild-type biofilms and tested whether we could alter the viscoelastic properties of engineered biofilms for biofabrication. We first examined the surface morphology of wild-type and TasA-HisTag biofilms and noted that the engineered biofilm was smoother than the typical wrinkled surface of the wild-type biofilm. Analysis with a goniometer revealed that the engineered biofilm was much more hydrophilic than the wild-type biofilm (water contact angle of 25.1±5.0° for TasA-HisTag biofilms vs 124.2±3.0° for the wild-type biofilm). The engineered biofilm was based on a ΔtasAΔsinRΔeps mutant strain (by removing the epsA~O gene cluster and tasA gene from the wild type strain), as anticipated the lack of the endogenous biofilm component pathways dramatically affected the hydrophobicity of the biofilms (reduced hydrophobicity). However we should point out that, if a future application requires more hydrophobicity, there are at least two approaches that can restore the hydrophobic properties of the biofilms: (i) adding those endogenous systems back into host strain, and/or (ii) functionalizing fusion domains onto TasA with hydrophobic features.

We next turned to fabricate biofilms into defined geometries using 3D printing technique. When we printed regular pentagon shapes using the wild-type and TasA-HisTag biofilms with the same printing conditions (nozzle diameter set to 160 μm), the lines of wild-type expanded to 500 μm as they were deposited, whereas the TasA-HisTag biofilm had the desired width (160 μm). Similar trends were found with other engineered biofilms, such as TasA-mefp5 and TasA-OPH biofilms, which all exhibited better printability than the wild type biofilm. Detailed rheological measurements and comparisons of the storage modulus (G', representing elastic deformation), loss modulus (G", representing viscous deformation) as well as the capacity of instantaneous recovery of the viscoelastic networks suggested that the relatively low viscoelasticity of the engineered biofilms made them more suitable for printing than wild type biofilm. Specifically, the internal network structures of the two hydrogel-like biofilms were subjected to similar compression when they were exposed to the extremely high pressures in the printer's cavity before they were extruded; however, the differential viscoelastic properties of the two biofilms would respond to this pressure discreetly: given its higher storage modulus and stronger instantaneous recovery capacity of their viscoelastic networks, the wild-type biofilm could be expected to possess better reversible deformability (shape recovery) than the engineered TasA biofilm and thus would exhibit "expanded" line feature as it was extruded. In addition, the richness of EPS polysaccharide components in the wild type biofilm may also contribute to the observed "expanded" line feature as they may promote moisture absorption[7,31], particularly considering that the WT biofilm might have the EPS components fully exposed to air as their hydrophobin protein layer could be completely disrupted during biofilm scraping and printing processes. Collectively, our results demonstrated that the viscoelastic properties of *B. subtilis* biofilms could be tunably altered and thus the engineered biofilms could be manipulated at high resolution for 3D printing applications.

We next explored the controllable geometry and functionality of our engineered *B. subtilis* biofilms by using several types of inorganic NPs. Specifically, *B. subtilis* biofilms containing TasA-HisTag nanofibers with diverse immobilized quantum dots (QDs) were used as building materials to fabricate well-defined shapes with 3D printing techniques. We prepared building materials in three colors by adding blue (CdZnS@ZnS), red (CdSeS@ZnS), and green (CdZnSeS@ZnS) QDs to TasA-Histag nanofiber biofilms. When printed into different 3D structures, such as polygons and letters, these cell/inorganic hybrid materials were blue, red, and green under UV light (350 nm) (FIG. 2; FIGS. 4A-4G). The fluorescence properties of these materials were confirmed by confocal fluorescent microscopy and fluorescence spectrometry.

Self-Regeneration, Encapsulation, and Viability of Living Functional Materials

One of the most attractive attributes of living materials is their ability to self-regenerate. To assess whether our engineered biofilms maintain this ability, we printed TasA-HisTag nanofiber biofilms into controlled hexagonal patterns on glass slides and then placed the printed biofilms in direct contact with a nutrient-rich agar plate (FIG. 3A). The biofilms regrew in hexagonal patterns after 2 days on agar plates. We then exposed the biofilm on the first agar plate to a second agar plate and found that the biofilm still grew in the initial hexagonal pattern, demonstrating the high fidelity, self-regenerative capacity of our engineered and printed biofilms (FIG. 3B). Remarkably, analysis of the viscoelastic properties of the regenerated biofilms showed that they had almost the same elastic and viscous modulus levels as the initially grown biofilms (FIG. 3C), a finding emphasizing that not only the genotype of a given biofilm but also its phenotypic features (including material properties) can be regenerated.

We next assessed the viability of hybrid functionalized biofilms. Preliminarily, we cultured control (biofilm-deficient), TasA, or TasA-HisTag biofilms in the presence of equal amounts of QDs and then monitored biofilms production. We found that the presence of QDs did not deleteriously affect the growth and production of TasA-HisTag biofilms; however, the QDs did inhibit the growth of both biofilm-deficient bacteria and biofilms lacking the HisTag modification. Moreover, TEM imaging further revealed that toxic QDs could be immobilized onto TasA-HisTag nanofibers avoiding direct contact with bacterial cells. These results implied that the HisTag could interact with and immobilize the QDs onto biofilms and thereby protect the functionalized biofilm from direct damage by these toxic nanoparticles. Indeed, a self-regeneration experiment testing regrowth on agar plates showed that the cells of hybrid functionalized biofilms remained viable after exposure to QDs. We also confirmed that our biofilms remained viable following various fabrication techniques, including printing into various shapes on glass and polyvinyl chloride (PVC) polymers, among others.

To further demonstrate the suitability of our engineered biofilms for biofabrication, we encapsulated the biofilms into geometrically predefined hydrogel compartments fabricated by two techniques: 3D printing and microencapsulation. We then evaluated both their functionality and their viability in these confined environments (FIG. 1C) by sequentially printing hydrogels and a strain that can produce a TasA-mCherry nanofiber biofilm. Specifically, the printed biofilm was sandwiched between two layers of hydrogels consisting of gelatin and sodium alginate, two common types of polymeric materials used for hydrogel formation[32, 33]. When immersed in minimal medium (MSgg) supplemented with 0.5 mM IPTG, the biofilm trapped inside the gel exhibited red fluorescence. Remarkably, the biofilms encapsulated in the hydrogels remained viable and functional even after 5 weeks (without any supplemental nutrition), inidicating that the biofilms produced with our platform can exhibit long-term viability and do not require extensive energy inputs, very attractive attributes for the practical application of living functional materials.

We next looked into the fabrication of engineered biofilms using microencapsulation technique, a technique that had previously been utilized for encapsulation of mammalian cells inside alginate-poly-(L-lysine)-alginate (APA) hydrogel microspheres[34, 35]. Here, using a standard microencapsulation protocol, we were able to produce uniform APA/$Ca^{2+}$ hydrogel microspheres (~400 microns) by mixing APA and cells (FIG. 3E left). The encapsulated cells could sense IPTG molecules, producing biofilms that exhibited red fluorescence. This result demonstrated that the biofilm retained its functionality in the APA/$Ca^{2+}$ microspheres (FIG. 3E). Thus, our programmable *B. subtilis* production platform can be used to produce functional and viable biofilms that are highly scalable, from simple growth in standard flasks and petri dishes, to complex printed geometries, and sophisticated microencapsulated environments.

Recent studies have reported the incorporation of genetically engineered bacteria into 3D printed hydrogels to create living wearable devices[16, 20, 29, 36], but their fabrication required the use of synthetic materials with appropriate viscoelastic properties because the printability of such living materials devices depended primarily on the rheological properties of the synthetic materials. In this regard, printable bacterial biofilms have intrinsic advantages over free bacterial cells. First, the cells in biofilms are held in place by the extracellular network and are thus in some sense immobilized and partially protected against harsh conditions[37, 38]. Second, the gel-like biofilms can be engineered to possess tunable viscoelastic properties that are fit for printing in their own right. We envision that our programmable *B. subtilis* biofilm production platform will be suitable for use in medical implants, biosensors, and drug-delivery devices, as these applications require the secretion of viscous proteins or protein drugs, or the functional capacity to express other useful molecules.

Living functional materials represent an opportunity to harness engineered biological systems for new capabilities. By leveraging the power of genetic engineering and the intrinsic advantage of the export machinery of *B. subtilis*, we have introduced a new living functional material platform based on *B. subtilis* biofilms. We engineered the extracellular amyloid-like protein TasA, a major subunit of the fibrous components of *B. subtilis* biofilms, by fusing it with various other proteins or protein domains to endow the living system with new functionalities. We used our platform to make programmable living materials exhibiting functional properties as diverse as intrinsic fluorescence, enzymatic activity, and the templated assembly of various functional inorganic NPs to perform hybrid enzyme/inorganic hybrid reaction cascades. We also made living materials that exhibit attractive viscoelastic properties and fabricated them into diverse shapes and microstructures, both on their own and with other polymeric gel materials, using 3D printing and micro-gel encapsulation techniques. Our programmable and printable *B. subtilis* biofilms therefore represent a new type of living functional material: they are multifunctional, self-regenerating, and tunable, and have considerable fabrication processability. As this new type of living functional material offers previously unattainable material performance properties relevant to manufacturing, our invention provides new classes of complex multifunctional materials and dynamic and regenerative nanotechnologies.

Strains and Plasmids

The original wild-type strain, *B. subtilis* 2569[39]. A mutant strain with both the tasA and sinR genes simultaneously knocked out (referred to as ΔtasAΔsinR) and a mutant strain with the tasA, sinR, and epsA~O genes knocked out (referred to as ΔtasAΔsinRΔeps) were constructed and sequenced. The original peptide insert regions were either fully synthesized (Genewiz) or PCR-generated. All cloning was performed following standard protocols of molecular cloning or isothermal Gibson Assembly and verified by DNA sequencing (Genewiz). All strains, plasmids, and primers used in this study are listed in Supplementary Tables 2 and 3. Gene sequences and amino acid sequences of TasA and fusion proteins are presented in Supplementary Tables 4 and 5, respectively.

Biofilm Culture Conditions

Seed cultures were grown in LB medium overnight at 37° C. Biofilm cultures were grown for 1-3 days at 30° C. in MSgg medium[23, 40] (5 mM potassium phosphate (pH=7)/100 mM Mops (pH 7)/2 mM $MgCl_2$/700 μM $CaCl_2$/50 μM $MnCl_2$/50 μM $FeCl_3$/1 μM $ZnCl_2$/2 μM thiamine/0.5% glycerol/0.5% glutamate/50 tryptophan/50 μg/ml phenylalanine), supplemented with 5 μg/mL chloramphenicol and 0.5 mM IPTG when necessary. For biofilm formation on agar plates, MSgg medium was solidified by the addition of 1.5% w/v Bacto agar (Difco), and the agar plates were cultured at 30° C.

Paraoxon Degradation with Engineered Biofilms

The degradation of paraoxon followed a two-step cascade of catalytic reactions, enabled by biofilms containing TasA-OPH nanofibers and TasA-HisTag nanofiber-templated assembly of nickel nitrilotriacetic acid (Ni-NTA) decorated AuNPs (abbreviated as AuNPs). Enzymatic activities of TasA-OPH biofilms or TasA-HisTag biofilm-assembled AuNPs were first confirmed using independent degradation experiments. The two-step catalytic reactions were executed sequentially, either in independent biofilm cultures or co-cultured biofilms.

Biofabrication of Engineered Biofilms Using 3D Printing

The cultured biofilms were scraped off the culture plates and placed (along with QDs when necessary) into the charging barrels. Three-dimensional structures (including polygon graphs or circles) were printed on glass, PVC plates, or gelatin hydrogel surfaces using a BioScaffolder3.1 3D printer (GeSim). For the bottom and top layers of the printed "sandwiched" biofilm structures, a mixture containing 5% gelatin and 2% sodium alginate was applied; the intermediate layer was the printed biofilm ink. The as-printed structures were submerged into a 500 mM $CaCl_2$ solution until the sodium alginate hydrogel solidified (i.e., turned white). The 3D hydrogels were then cultured in MSgg medium supplemented with IPTG. The morphology of the printed structures was imaged with a Nikon SMZ25 stereoscopic microscope.

Biofabrication of Engineered Biofilms Via Microencapsulation

A B-395 Pro encapsulator (BÜCHI Labortechnik AG,) was used to fabricate microencapsulated cells of the transgenic *B. subtilis* strain as alginate-poly-(L-lysine)-alginate microbeads (APA beads, 400 μm diameters) as previously described[35]. The as-fabricated APA microbeads containing the transgenic *B. subtilis* strain were cultured in MSgg and the samples were then collected to assess cell viability and functional performance, observed with a Nikon ECLIPSE Ti fluorescence microscope.

Transmission Electron Microscopy (TEM) and Immuno-Gold Labeling

TEM sample preparation and imaging: Carbon-coated TEM grids (Zhongjingkeyi Technology, EM Sciences) were placed on top of a 20 μL solution droplet containing biofilm liquid culture for 1-5 min. The grids were washed by 20 μL PBS buffer and 20 μL water. The excess liquid was blotted off on a Whatman no. 1 filter paper, and the sample was negatively stained with 20 μL 1 w/v % uranyl acetate solution. The samples were air dried and examined in a FEI T12 transmission electron microscope at an accelerating voltage of 120 kV. Images were taken with an AMT 2 k CCD camera.

For immunolocalization of TasA, diluted samples on nickel grids were floated on blocking buffer consisting of 1% skim milk in PBS with 0.1% Tween 20 for 30 min, incubated for 2 h with anti-TasA primary antibody diluted 1:150 in blocking buffer[23]. Afterwards, the samples were rinsed in PBST (PBS with 0.1% Tween 20) and exposed to goat anti-rabbit 20-nm gold secondary antibody (Ted Pella, Inc.) for 1 h, rinsed with water, and treated with the same conditions as the aforementioned TEM samples. All grids were stained with uranyl acetate and lead citrate. TEM imaging was performed following the protocol described above.

Reverse Phase High-Performance Liquid Chromatography (RP-HPLC) Analysis

RP-HPLC was used for monitoring PAR and MHET and their associated degradation products.

RP-HPLC was performed on an Agilent 1260 Infinity system (Agilent Technologies) equipped with a ZORBAX SB-C18 guard column (4.6×12 5 mm, 5 μm) and a ZORBAX SB-C18 analytical column (4.6×150 mm, 5 μm) from Agilent Technologies. The mobile phase was methanol/20 mM phosphate buffer (pH=2.5) at a flow rate of 1.0 mL/min, and the effluent was monitored at a wavelength of 240 nm with a UV detector. The typical elution condition was as follows: 0 to 15 min, 25% (v/v) methanol; 15 to 25 min, 25-95% methanol linear gradient; 25 to 30 min, 95-25% methanol linear gradient.

MHET Degradation with Engineered Biofilms

ΔtasAΔsinRΔeps/TasA-MHETase biofilms ($OD_{600}$=1) were incubated with 400 μM of MHET in 40 mM $Na_2HPO_4$—HCl (pH=7.0), 80 mM NaCl, at 30° C. for 18 hours. The reaction was stopped by adding an equal amount of 160 mM phosphate buffer (pH=2.5) containing 20% (v/v) DMSO. The MHET and its degradation product, TPA, were analyzed with RP-HPLC as described above.

Contact Angle Measurement

Biofilms grown on MSgg agar plates were carefully isolated, and the contact angle of these biofilms was then measured at room temperature using a Theta Lite optical tensiometer (Biolin) following the sessile drop method[41].

Assessment of Rheological Properties

Both strain sweep experiments and frequency sweep experiments were performed to assess the rheological properties of engineered biofilms using a strain-controlled rheometer (Anton paar MCR101) equipped with a 24.948 mm diameter cone.

Fluorescence Microscopy

The ΔtasAΔsinRΔeps/TasA-mCherry biofilms and the as-printed samples containing ΔtasAΔsinRΔeps/TasA-HisTag biofilms anchored with diverse QDs (including blue (CdZnS@ZnS), red (Co-NTA CdSeS@ZnS), and green QDs (CdZnSeS@ZnS) were collected for fluorescent imaging. If not specifically noted, all imaging was performed using Laser Scanning Confocal Microscopy LSM 710 (Zeiss). The fluorescent imaging of 3D printed hydrogels containing TasA-mCherry biofilms was carried out with a Nikon SMZ25 stereoscopic microscope.

Fluorescence Spectra Measurement

Fluorescence spectra of biofilms/QDs complex structures were collected using a HORIBA FL-3 Spectrofluorometer with excitation of 350 nm light.

Statistical Analysis

Data are presented as means±s.d. (standard deviation). The values of s.d. were calculated based on three replicates. A Student's t-test was used to compare means of sample groups, and P-values less than 0.05 were considered to be statistically significant.

REFERENCES

1. Chen, A. Y. et al. Synthesis and patterning of tunable multiscale materials with engineered cells. Nat Mater 13, 515-523 (2014).
2. Nguyen, Peter Q., et al. Engineered Living Materials: Prospects and Challenges for Using Biological Systems to Direct the Assembly of Smart Materials. Adv Mater 30(19), 1704847 (2018).
3. Ball P. Synthetic biology—Engineering nature to make materials. MRS Bulletin 43(7): 477-484 (2018).
4. Y. Wang, et al. Emerging Paradigms for Synthetic Design of Functional Amyloids. Journal of Molecular Biology (2018)
5. Tallawi, M., Opitz, M. & Lieleg, O. Modulation of the mechanical properties of bacterial biofilms in response to environmental challenges. Biomater Sci 5, 887-900 (2017).
6. Barnhart, M. M. & Chapman, M. R. Curli biogenesis and function. Annu Rev Microbiol 60, 131-147 (2006).
7. Vlamakis, H., Chai, Y., Beauregard, P., Losick, R. & Kolter, R. Sticking together: building a biofilm the *Bacillus subtilis* way. Nat Rev Microbiol 11, 157-168 (2013).
8. DeBenedictis, E. P., Liu, J. & Keten, S. Adhesion mechanisms of curli subunit CsgA to abiotic surfaces. Sci Adv 2, e1600998 (2016).
9. Edwards, S. J. & Kjellerup, B. V. Applications of biofilms in bioremediation and biotransformation of persistent organic pollutants, pharmaceuticals/personal care products, and heavy metals. Appl Microbiol Biotechnol 97, 9909-9921 (2013).
10. Donato, V. et al. *Bacillus subtilis* biofilm extends *Caenorhabditis elegans* longevity through downregulation of the insulin-like signalling pathway. Nat Commun 8, 14332 (2017).
11. Hobley, L., Harkins, C., MacPhee, C. E. & Stanley-Wall, N. R. Giving structure to the biofilm matrix: an overview of individual strategies and emerging common themes. FEMS Microbiol Rev (2015).
12. Yates, M. D. et al. Measuring conductivity of living Geobacter sulfurreducens biofilms. Nat Nanotechnol 11, 910-913 (2016).
13. Cao, Y. X. L. et al. Programmable assembly of pressure sensors using pattern-forming bacteria. Nature Biotechnology 35, 1087-+(2017).

14. Wang, X. P., J.; An, B.; Li, Y.; Shang, Y.; Ning, Z.; Liu, Y.; Ba, F.; Zhang, J.; Zhong C. Programming cells for dynamic assembly of inorganic nano-objects with spatiotemporal control. Adv Mater 1705968 (2018).
15. Nguyen, P. Q., Botyanszki, Z., Tay, P. K. & Joshi, N. S. Programmable biofilm-based materials from engineered curli nanofibres. Nat Commun 5, 4945 (2014).
16. Liu, X. et al. Stretchable living materials and devices with hydrogel-elastomer hybrids hosting programmed cells. Proc Natl Acad Sci USA 114, 2200-2205 (2017).
17. Liu, L. et al. Developing *Bacillus* spp. as a cell factory for production of microbial enzymes and industrially important biochemicals in the context of systems and synthetic biology. Applied Microbiology and Biotechnology 97, 6113-6127 (2013).
18. Kesel, S. et al. Direct comparison of physical properties of *Bacillus subtilis* NCIB 3610 and B-1 biofilms. Applied and environmental microbiology 82, 2424-2432 (2016).
19. Cairns, L. S., Hobley, L. & Stanley-Wall, N. R. Biofilm formation by *Bacillus subtilis*: new insights into regulatory strategies and assembly mechanisms. Molecular Microbiology 93, 587-598 (2014).
20. Liu, X. et al. 3D Printing of Living Responsive Materials and Devices. Adv Mater (2017).
21. Driks, A. Tapping into the biofilm: insights into assembly and disassembly of a novel amyloid fibre in *Bacillus subtilis*. Mol Microbiol 80, 1133-1136 (2011).
22. Diehl, A. et al. Structural changes of TasA in biofilm formation of *Bacillus subtilis*. Proc Natl Acad Sci USA 115, 3237-3242 (2018).
23. Romero, D., Aguilar, C., Losick, R. & Kolter, R. Amyloid fibers provide structural integrity to *Bacillus subtilis* biofilms. Proceedings of the National Academy of Sciences 107, 2230-2234 (2010).
24. Chai, L. et al. Isolation, characterization, and aggregation of a structured bacterial matrix precursor. Journal of Biological Chemistry 288, 17559-17568 (2013).
25. Zakeri, B. et al. Peptide tag forming a rapid covalent bond to a protein, through engineering a bacterial adhesin. Proceedings of the National Academy of Sciences of the United States of America 109, E690-E697 (2012).
26. Yoshida, S. et al. A bacterium that degrades and assimilates poly(ethylene terephthalate). Science 351, 1196-1199 (2016).
27. Botyanszki, Z., Tay, P. K., Nguyen, P. Q., Nussbaumer, M. G. & Joshi, N. S. Engineered catalytic biofilms: Site-specific enzyme immobilization onto *E. coli* curli nanofibers. Biotechnol Bioeng 112, 2016-2024 (2015).
28. Slavin, Y. N., Asnis, J., Hafeli, U. O. & Bach, H. Metal nanoparticles: understanding the mechanisms behind antibacterial activity. J Nanobiotechnology 15, 65 (2017).
29. Schaffner, M., Ruhs, P. A., Coulter, F., Kilcher, S. & Studart, A. R. 3D printing of bacteria into functional complex materials. Sci Adv 3, eaao6804 (2017).
30. Gladman, A. S., Matsumoto, E. A., Nuzzo, R. G, Mahadevan, L. & Lewis, J. A. Biomimetic 4D printing. Nat Mater 15, 413-418 (2016).
31. Flemming H C, Wingender J. The biofilm matrix. Nat Rev Microbiol 8(9): 623 (2010).
32. Luo, Y., Lode, A. & Gelinsky, M. Direct plotting of three-dimensional hollow fiber scaffolds based on concentrated alginate pastes for tissue engineering. Adv Healthc Mater 2, 777-783 (2013).
33. Connell, J. L., Ritschdorff, E. T., Whiteley, M. & Shear, J. B. 3D printing of microscopic bacterial communities. Proc Natl Acad Sci USA 110, 18380-18385 (2013).
34. Orive, G, Tam, S. K., Pedraz, J. L. & Halle, J. P. Biocompatibility of alginate-poly-L-lysine microcapsules for cell therapy. Biomaterials 27, 3691-3700 (2006).
35. Xue, S. et al. A Synthetic-Biology-Inspired Therapeutic Strategy for Targeting and Treating Hepatogenous Diabetes. Mol Ther 25, 443-455 (2017).
36. Lehner, B. A., Schmieden, D. T. & Meyer, A. S. A Straightforward Approach for 3D Bacterial Printing. ACS Synth Biol (2017).
37. Wincing, J. N., Angelini, T. E., Seminara, A., Brenner, M. P. & Weitz, D. A. Biofilms as complex fluids. Mrs Bulletin 36, 385-391 (2011).
38. Flemming, H. C. et al. Biofilms: an emergent form of bacterial life. Nat Rev Microbiol 14, 563-575 (2016).
39. Konkol, M. A., Blair, K. M. & Kearns, D. B. Plasmid-encoded ComI inhibits competence in the ancestral 3610 strain of *Bacillus subtilis*. J Bacteriol 195, 4085-4093 (2013).
40. Branda, S. S., Gonzalez-Pastor, J. E., Ben-Yehuda, S., Losick, R. & Kolter, R. Fruiting body formation by *Bacillus subtilis*. Proc Natl Acad Sci USA 98, 11621-11626 (2001).
41. Arnaouteli, S. Bifunctionality of a biofilm matrix protein controlled by redox state. Proceedings of the National Academy of Sciences of the United States of America 114, E6184-E6191 (2018).
42. Hochuli, E., Bannwarth, W., Dobeli, H., Gentz, R. & Stuber, D. Genetic Approach to Facilitate Purification of Recombinant Proteins with a Novel Metal Chelate Adsorbent. Nat. Biotech 6, 1321-1325 (1988).
43. Zhong, C. et al. Strong underwater adhesives made by self-assembling multi-protein nanofibres. Nat Nanotechnol 9, 858-866 (2014).
44. Arakaki, A., Webb, J. & Matsunaga, T. A novel protein tightly bound to bacterial magnetic particles in Magnetospirillum magneticum strain AMB-1. Journal of Biological Chemistry 278, 8745-8750 (2003).
45. McEvoy, A. L. et al. mMaple: a photoconvertible fluorescent protein for use in multiple imaging modalities. PLoS One 7, e51314 (2012).
46. Shaner, N. C. et al. Improved monomeric red, orange and yellow fluorescent proteins derived from Discosoma sp. red fluorescent protein. Nat Biotechnol 22, 1567-1572 (2004).
47. Lu, H. D., Wheeldon, I. R. & Banta, S. Catalytic biomaterials: engineering organophosphate hydrolase to form self-assembling enzymatic hydrogels. Protein Engineering Design & Selection 23, 559-566 (2010).

SUPPLEMENTARY INFORMATION

1. Strain Construction

*Bacillus subtilis* 2569 ΔtasAΔsinR and *Bacillus subtilis* 2569 ΔtasAΔsinRΔEps Mutants To create biofilm-defective strains, we first constructed two suicide plasmids, pMAD-ΔtasAsinR and pMAD-Δeps. Primer pairs of sal-dAF/dcAR were used to amplify the 1 kb fragment from the genome of wild-type strain on the upstream of tasAsinR gene (sinR and tasA genes are next to each other). Primer pairs of daCF/bgl-dCR were used to amplify the 1 kb fragment on the downstream of tasAsinR gene. The two fragments were fused together into a 2 kb fragment (resulting in deletion of the target tasAsinR gene), which was then inserted into pMAD by SalI/BglII digestion to obtain the suicide plasmid pMAD-ΔtasAΔsinR.

Similarly, primer pairs of Bam-d EPS A up F/d EPS A up R, and d EPS 0 dw F/Sal-d EPS 0 dw R were used to amplify the 1 kb fragment on the upstream and downstream of the epsA~O gene cluster, respectively. The two fragments were then fused together into a 2 kb fragment (resulting in deletion of the target epsA~O gene cluster), which was then inserted into the pMAD at the BamHI/SalI site to obtain the suicide plasmid pMAD-Δeps.

The suicide plasmids were then transformed into *B. subtilis* competent cells respectively, replacing the BamHI/SalI site to free this antibiotic selection marker as previously described[1]. *B. subtilis* 2569 strain transformed with suicide plasmids was selected on LB erythromycin agar plate at 30° C. Transformants were restreaked onto non-selective LB and grown overnight at 42° C. Isolates were patched onto LB agar supplemented with erythromycin at 5 μg/mL. PCR fragments from the genomic DNA of mutants were sequenced to confirm the deletions of tasAsinR gene and epsA~O gene cluster. The resultant mutant strains used in this study were referred to as *B. subtilis* 2569 ΔtasAΔsinR (ΔtasAΔsinR) and *B. subtilis* 2569 ΔtasAΔsinRΔeps (ΔtasAΔsinRΔeps), respectively.

2. Plasmid Construction

The plasmids used in this study were constructed with standard molecular cloning techniques using Gibson assembly kit or restriction endonucleases, T4 DNA Ligase. A Bio-Rad S1000 Thermal Cycler with Dual 48/48 Fast Reaction Modules (Bio-Rad) was used to perform PCRs, ligations, and restriction digests. Gel extractions were carried out with QIAquick Gel Extraction Kits (Qiagen). Custom oligonucleotide primers were ordered from GENEWIZ.

All ligations for plasmid construction were transformed into *E. coli* strain DH5αPRO with standard protocols. Isolated colonies were inoculated into LB medium (Fisher) supplemented with 50 μg/ml carbenicillin. Plasmids were extracted with QiagenQIAprep Spin Miniprep Kits. Plasmid construct sequences were confirmed by restriction digest and sequencing was performed by Genewiz. The parts that constitute the plasmids used in this work are described in Supplementary Table 2.

Plasmids for expressing genes from the grac promotor were constructed by using a pHT01 empty plasmid as a starting point. Primers for tasA were designed based on the *B. subtilis* 168 genome sequence, and tasA fragment was amplified from the *B. subtilis* 2569 genome template. Genes for fusion protein R were synthesized by Genewiz and optimized for *B. subtilis* host expression. The tasA and R genes were connected with linker gene fragments corresponding to GGGSGGGS (SEQ ID NO:01) or GGGGSGGGGS (SEQ ID NO:02) during gene synthesis or PCR processes. Those tasA-R gene fragments were then inserted into the pHT01 plasmid at BamHI/SmaI sites or single SmaI site. The constructed plasmids were named as pHT01-tasA-R vectors in this study. All the primers used were listed as Supplementary Table 3.

3. *Bacillus subtilis* Biofilms Culture

Solution-Based Biofilm Formation

Strains were inoculated from frozen glycerol stocks and grown in LB medium supplemented with 5 μg/mL chloramphenicol. Seed cultures were grown overnight at 37° C. The collected cell pellets after centrifugation were then resuspended in MSgg medium supplemented with 5 μg/mL chloramphenicol and 0.5 mM IPTG at an initial cell density of $5\times10^7$ cells/mL. The static liquid biofilm cultures were grown at 30° C. for 2-3 days.

Compositions of Luria-Bertani (LB) broth: 1% tryptone (Difco), 0.5% yeast extract (Difco), 1% NaCl. Compositions of MSgg broth: 100 mM morpholino propanesulfonic acid (MOPS) (pH 7), 0.5% glycerol, 0.5% glutamate, 5 mM potassium phosphate (pH 7), 50 μg/mL tryptophan, 50 μg/mL phenylalanine, 2 mM $MgCl_2$, 700 μM $CaCl_2$, 50 μM $FeCl_3$, 50 μM $MnCl_2$, 2 μM thiamine, 1 μM $ZnCl_2$.

3. Solid Plate-Based Biofilm Formation:

For solid-plate culture, liquid MSgg media were solidified through addition of Bacto agar (Difco) to 1.5%. Strains were inoculated from frozen glycerol stocks and grown in LB medium supplemented with 5 μg/mL chloramphenicol. Seed cultures were grown overnight at 37° C. The collected pellets through centrifugation were then resuspended in MSgg medium supplemented with 5 μg/mL chloramphenicol and 0.5 mM IPTG at an initial cell density of $5\times10^7$ cells/mL. 5-10 mL of the above cell resuspension solution was then placed on solid MSgg plate supplemented with 5 μg/mL chloramphenicol and 0.5 mM IPTG and then grown at 30 degrees for 2-3 days.

Antibiotics for *B. subtilis* culture were MLS (1 μg/mL erythromycin, 25 μg/mL lincomycin) or 5 μg/mL erythromycin; spectinomycin (100 μg/mL); chloramphenicol (5 μg/mL); Antibiotics for *E. coli* culture was Carbenicillin (50 μg/mL).

4. Crystal Violet (CV) Biofilm Assays

Quantification of biofilms was carried out following a Crystal violet (CV) staining protocol described in previous publications[2,3]. Experiments were first performed to verify that *B. subtilis* 2569 ΔtasAΔsinRΔeps/tasA-R formed thick biofilms upon IPTG induction in solution-based biofilm culture conditions. ΔtasAΔsinRΔeps/tasA-R cells, at an initial seeding density of $5\times10^7$ cells/mL, were grown in 24-well plate wells for 48 h at 30° C. in MSgg supplemented without or with 0.5 mM IPTG. Biofilms containing TasA-R nanofibers were collected by centrifugation at 5000 g for 10 mM The collected biofilms were washed in $ddH_2O$ and then recollected by centrifugation at 5000 g for 10 mM The samples were then added with 400 μL of 0.1% aqueous crystal violet (Sigma), and incubated at room temperature for 10-15 mM The samples were then washed for 3-4 times by immersing the samples in a tub of $ddH_2O$ until all visible dye was washed off. The washed samples were then recollected by centrifugation at 5000 g for 10 mM and added with 400 μL of 30% acetic acid aqueous solution and incubated for 10-15 mM at RT to solubilize the added CV. Subsequently, 125 μL of the solution was transferred to a 96-well plate well. Absorbance at 550 nm was measured, with 30% acetic acid aqueous solution used as a blank 5. Anti-TasA Immuno-Labelling Assay For immunolocalization of TasA proteins, biofilm samples (from two-day liquid culture) were first placed on nickel grids and then immersed in 20 μL blocking buffer (PBS buffer containing 1% skim milk and 0.1% Tween 20) for 30 min, followed by incubation for 2 h in 20 μL droplet of blocking buffer with anti-TasA primary antibody diluted at 1:150 ratio. Afterwards, the samples were rinsed 3 times in 20 μL PBST (PBS buffer containing 0.1% Tween 20) and subsequently transferred to 20 μL, droplet of blocking buffer with goat anti-rabbit secondary antibody conjugated to 20-nm gold particles diluted at 1:5000 ratio (Ted Pella, Inc.), where it was incubated for 1 h. The grids were then washed with 20 μL PBS buffer and 20 μL $ddH_2Q$. The excess liquid was blotted off on a filter paper (Whatman no. 1) and the sample was stained with 20 μL uranyl acetate (1-2% aqueous solution). The air-dried samples were eventually examined in a FEI T12 transmission electron microscope at an accelerating voltage of 120 kV. Images were taken with an AMT 2 k CCD camera.

6. Transmission Electron Microscopy (TEM)

Carbon-coated TEM grids (Zhongjingkeyi Technology, EM Sciences) were placed on top of 20 μL solution droplet containing biofilms from liquid culture (2-day or 3-day culture samples) for 5 min. The grids were washed by 20 μL PBS buffer and 20 μL water. The excess liquid was blotted off on a filter paper (Whatman no. 1) and the sample was stained with 20 μL uranyl acetate (1-2% w/v aqueous solution). The samples were air dried and examined in a FEI T12 transmission electron microscope at an accelerating voltage of 120 kV. Images were taken with an AMT 2 k CCD camera. To image and compare the TasA-R nanofibres of the differently functionalized biofilms, 3-day liquid culture samples were applied to ensure the observation of matured TasA-R nanofibers.

TEM imaging was also used to probe whether biofilms containing TasA-HisTag nanofibres were able to anchor nickel nitrilotriacetic acid-decorated gold nanoparticle (Ni-NTA-AuNP). Specifically, 20 μL droplet of sample was carefully added on top of the 200-mesh formvar/carbon-coated nickel TEM grids (Electron Microscopy Sciences) placed on a piece of parafilm for 2 min. The TEM grids were rinsed 3-4 times with a 30 μL droplet of $ddH_2O$ and 30 μL droplet of the selective binding buffer (1×PBS, supplemented with 0.487 M NaCl, 80 mM imidazole, and 0.2% v/v Tween 20), and then placed face-down in a 60 μL droplet of selective binding buffer with 10 nM 5 nm Ni—NTA-AuNP particles (Nanoprobes). The TEM grid on parafilm was covered with a petri dish to minimize evaporation and allowed to incubate for 90 min. The grid was then washed 5 times with selective binding buffer without Ni—NTA-AuNP particles, then twice with 1×PBS and twice with $ddH_2O$. The thoroughly washed grid was placed face-down on a droplet of filtered 2% uranyl acetate for 15-30 s. Excess uranyl acetate was wicked off with a piece of filter paper. The grid was then allowed to air dry. Images were obtained on a FEI Tecnai Spirit transmission electron microscope operated at 120 kV accelerating voltage.

7. Fluorescence Microscopy

To verify the functional properties of biofilms containing TasA-mCherry nanofibres or TasA-SpyTag nanofibres, fluorescence imaging was performed using Nikon confocal microscope A1R and Zeiss Axio Imager 2. The fluorescence images were acquired with the use of 587 and 488 nm channels for red and green fluorescence, respectively.

*B. subtilis* 2569 ΔtasAΔsinRΔeps/TasA-mCherry (ΔtasAΔsinRΔeps/TasA-mCherry) strain was inoculated from frozen glycerol stocks and grown in LB medium using 5 μg/mL chloramphenicol. Seed cultures were grown for 12 h at 37° C. Static biofilm cultures were grown at 30° C. in MSgg medium supplemented with 5 μg/mL chloramphenicol and 0.5 mM IPTG. A control group was carried out under the same condition, but without IPTG added in the medium. After 2-day cultivation, biofilms were harvested and concentrated. 10 μL of biofilm solution dripped on a glass slide was then imaged under Nikon confocal microscope AIR.

*B. subtilis* 2569 ΔtasAΔsinRΔeps/TasA-SpyTag (ΔtasAΔsinRΔeps/TasA-SpyTag) strain was inoculated from frozen glycerol stocks and grown in LB medium using 5 μg/mL chloramphenicol. Seed cultures were grown for 12 h at 37° C. Static biofilm cultures were grown at 30° C. in MSgg medium supplemented with 5 μg/mL chloramphenicol and 0.5 mM IPTG. A control group was carried out under the same condition, but without IPTG added in the medium. After 2-day cultivation, biofilms were harvested and resuspended with PBS in a tube. 0.5 mL 1 mg/mL purified SpyCatcher-GFP proteins in PBS was added in tubes, incubated for 1 h and then washed 3 times with PBS buffer. 10 μL of the mixture solution dripped on a slide was then imaged under Zeiss Axio Imager 2.

To further confirm the specific binding of SpyCatcher-GFP with biofilms through the SpyTag-SpyCatcher covalent interaction, we compared the fluorescence of three samples: TasA-SpyTag biofilm added with SpyCatcher-GFP protein, TasA-SpyTag biofilm added with free GFP protein, and TasA-HisTag biofilm added with SpyCatcher-GFP protein). Specifically, static liquid biofilm cultures were grown at 30° C. in MSgg medium supplemented with 5 μg/mL chloramphenicol and 0.5 mM IPTG. After 2-day cultivation, biofilms were harvested and resuspended with PBS in a tube. 0.5 mL 1 mg/mL purified SpyCatcher-GFP proteins in PBS was added in 1 mg TasA-SpyTag biofilm and 1 mg TasA-HisTag biofilm, respectively. 0.5 mL 1 mg/mL purified GFP proteins in PBS was added in 1 mg TasA-SpyTag biofilm. The samples were incubated for 1 h and then washed 3 times with PBS buffer. 10 μL of the mixture solution dripped on a slide was then imaged under Zeiss Axio Imager 2.

8. Fluorescence Spectra

Fluorescence features of the biofilms/QDs hybrid structures were characterized using a fluorescence spectrometer. 1 g of the ΔtasAΔsinRΔeps/TasA-HisTag biofilms were added with 200 μL QDs (Blue (CdZnS@ZnS), red (CdSeS@ZnS) or green (CdZnSeS@ZnS) QDs) to produce biofilm/QDs hybrid structures. 10 mg of the above samples were then coated on a glass plate. Fluorescence spectra of the coated samples were collected using HORIBA FL-3 at an excitation wavelength of 350 nm.

9. Paraoxon Degradation Through Enzyme/AuNPs Hybrid Biocatalysis System

The degradation of paraoxon followed two steps of catalysis reactions, enabled by biofilms containing TasA-OPH nanofibres and TasA-HisTag nanofibres-immobilized nickel nitrilotriacetic acid (Ni-NTA) decorated gold nanoparticles (abbreviated as AuNPs).

The full wavelength scanning for the PAR, PNP and PAP were done with a carry 5000 UV-Vis-NIR Spectrophotometer. The maximum absorption wavelength for PAR, PNP, and PAP was determined at 290, 405, and 230 nm respectively by UV spectra. The three compound PAR, PNP and PAP in the co-cultured system was assayed respectively by reverse phase high-performance liquid chromatography (RP-HPLC).

(1) Degradation of PAR into PNP with Biofilms Containing TasA-OPH Nanofibres

Biofilms containing TasA-OPH nanofibres from liquid culture were collected by centrifugation at 5000 rpm for 10 mM and resuspended in ches buffer (2-(N-Cyclohexylamino) ethane sulfonic acid, sigma C2885, pH=7.5), supplemented with 50 μM $CoCl_2$ (final OD=1). After 1 h incubation at 30° C., the pellets were harvested by centrifugation (5000 rpmx10 min) and resuspended in ches buffer (final OD=4, pH=10). For each assay, 900 μL of test sample was mixed with 100 μL of 10 mM paraxon in 10% methanol. The reaction mixtures were incubated at 37° C. for 2 h. Samples were taken every 10 minutes to monitor the absorbance of paranitrophenol from the hydrolysis of substrate (paraoxon) at 405 nm using the Biotec Cytation 5 imaging reader.

The enzymatic kinetics of OPH follows Michaelis-Menten equation:

$$V = \frac{S * Vmax}{Km + 2}$$

The kinetic parameters, Vmax and Km, were measured by using Lineweaver-Burk equation;

In the linearization of Michaelis-Menten equation:

$$\frac{1}{V} = \frac{Km}{S*Vmax} + \frac{1}{Vmax}$$

V is reaction velocity,

Vmax is the maximum reaction velocity,

S is the concentration of substrate, and Km is Michaelis constant.

Vmax and Km were obtained as 0.0602 mM/min and 0.2891 mM, respectively.

(2) PNP Reduction Based on Functional Assessment for TasA-HisTag Nanofibres-Anchored AuNPs Biofilms

*B. subtilis* 2569 ΔtasAΔsinRΔeps/TasA-HisTag (ΔtasAΔsinRΔeps/TasA-HisTag) strain was inoculated from frozen glycerol stocks and grown in LB medium using 5 μg/ml chloramphenicol. Seed cultures were grown for 12 h at 37° C., shaking at 220 rpm. Biofilm cultures were grown at 30° C. in MSgg medium supplemented with 5 μg/mL chloramphenicol, 0.5 mM IPTG and 100 μL 5 nM Ni-NTA-AuNPs in a 12-well plate. After 2-3 days cultivation, biofilms were harvested and resuspended in PBS buffer (OD=1) after washing with 10 mL PBS buffer for 3-5 times. The reaction solution was prepared by mixing 4 mL of 1 mM PNP, 100 μL of 2 M $NaBH_4$, and 900 μL of the PBS buffer containing TasA-HisTag biofilms. The PNP concentration over reaction time was monitored based on the absorbance peak at 405 nm using the Biotec Cytation 5 imaging reader. Samples without addition of IPTG or without addition of Ni—NTA-AuNPs (abbreviated as AuNPs) were used as control groups.

The reduction of paranitrophenol follows a first-order reaction and the reaction kinetic can be described by the equation below:

$$d[A]/dt=k[A]$$

When t=0, $[A]=[A_0]$, $[A_0]$ is the original starting concentration of reactant A, The relationship in the concentration of Aover time can be written as:

$\ln (A/A_0)=k\,t$, where k is the chemical reaction rate constant.

The reaction rate equation for all cases can be described with the following equations:

TH(IPTG ON)+AuNPs+NaBH4+PNP: $y=0.06708x+0.03788$

TH(IPTG ON)+AuNPs+NaBH4+PNP: $y=0.02211x-0.00892$

TH(IPTG ON)+NaBH4+PNP: $y=0.00218x+0.00037$

PNP: $y=-0.00020x+0.00508$

The results revealed that the reaction system in the case of TasA-His, with both AuNPs and $NaBH_4$ present, has the highest rate constant and thus the highest efficiency to degrade PNP.

(3) Biocatalytic Cascade Degradation of Paraoxon Through Independently Cultured Biofilms 2 mL of 10 mM paraxon in 10% methanol was added to 18 mL 0.1 M ches buffer solution containing TasA-OPH biofilms (OD=4, pH=10) and 50 μM $CoCl_2$ solution and incubated at 37° C. Samples were taken every 20 minutes to monitor the absorbance of paranitrophenol from the hydrolysis of substrate (paraoxon) at 405 nm using the Biotec Cytation 5 imaging reader. After 2 h, 10 mL samples were centrifuged to collect the supernatant.

After 2-day cultivation, biofilms containing TasA-HisTag nanofibres were harvested and washed with copious amount of PBS buffer for 3-5 times and then resuspended in PBS buffer (OD=1). The reaction solution was prepared by adding 8 mL of the supernatant (collected from step 1), 1 mL of 2 M $NaBH_4$, and 1 mL of the PBS buffer containing TasA-HisTag biofilms. The reaction mixtures were incubated at room temperature. Samples were taken every 20 minutes, the PNP degradation was monitored with the absorbance peak at 405 nm using the Biotec Cytation 5 imaging reader.

(4) Biocatalytic cascade degradation of paraoxon through co-cultured biofilm systems ΔtasAΔsinRΔeps/TasA-OPH and ΔtasAΔsinRΔeps/TasA-HisTag strains were inoculated from frozen glycerol stocks and independently grown in 50 mL LB medium supplemented with 5 μg/mL chloramphenicol for 12 h at 37° C. Cell pellets from the above culture were pelleted, and equal amount of cells were mixed in small amount of MSgg medium. The mixture was then added to 50 mL MSgg medium supplemented with 5 μg/mL chloramphenicol, 0.5 mM IPTG and 5 nM AuNPs. The culture was then grown at 30° C. for 2-3 days to form single, hybrid biofilms.

After 2-3 days cultivation, biofilms were harvested and resuspended in ches buffer (pH=7.5), supplemented with 50 μM $CoCl_2$ (OD=1). After 1 h incubation at 30° C., the pellets were harvested and resuspended into pH=10 ches buffer (OD=4). 2 mL of 10 mM paraxon in 10% methanol was mixed with 18 mL of the hybrid biofilm sample and incubated at 37° C. Samples were taken every 20 minutes to monitor the absorbance of paranitrophenol at 405 nm using the Biotec Cytation 5 imaging reader. After 2 h, 1 mL of 2M $NaBH_4$ were added to 9 mL of the above samples, reaction mixtures were then incubated at room temperature. Samples were taken out every 20 minutes and the PNP concentration was monitored based on the characteristic absorbance peak at 405 nm using the Biotec Cytation 5 imaging reader.

10. Rheology Measurement

The rheological properties of engineered biofilms were performed on a strain-controlled rheometer (Anton paar MCR101) equipped with a 24.948 mm diameter cone-plate (48 pin gap). All biofilm samples were scraped from MSgg plate and placed on the cone plate. To minimize water evaporation in biofilms, a closed surrounding chamber containing pure water was used. To determine the linear viscoelastic region of the biofilm samples, strain sweep experiments from 0.01~100% strain amplitude were performed at a fixed frequency of 1 rad/s. Frequency sweep experiments from 100 to 0.01 rad/s were performed at 1% strain amplitude. The temperature was kept at a constant temperature of 25° C. throughout the experiments with a Peltier thermoelectric device.

Instantaneous recovery capacity of the viscoelastic networks of the WT and TasA-HisTag biofilms were measured by an oscillatory time sweep (0.1% amplitude strain, 5 rad/s angular frequency) for 120 s, followed by a sudden shear process in a steady state (100 $s^{-1}$) for 120 s and an oscillatory time sweep (0.1% amplitude strain, 5 rad/s angular frequency) for another 120 s.

11. 3D Printing Experiments (1) 3D Printing of Biofilms

Strains were cultured on MSgg plates for 2-3 days. The as-grown biofilms were scraped off from the plates and placed into the charging barrels. 3D structures of variable shapes were printed using a robotic 3D printer (GeSim BioScaffolder 3.1). The shapes of polygons or circles were directly printed using the existing graph program in the system, while other shapes such as letters representative of ShanghaiTech University were printed using the imported stl graph program. The printing parameters applied in the experiments were: printing pressure (150-250 kPa), the inner diameter of nozzle (160 μm), and printing speed (5-10 mm/s).

(2) 3D Printing of Biofilms/QDs Hybrid Structures.

ΔtasAΔsinRΔeps/TasA-HisTag biofilms were cultured on MSgg plates for 2-3 days. Blue (CdZnS@ZnS), red (CdSeS@ZnS) and green (CdZnSeS@ZnS) QDs were added in the culture media from the start. The as-grown biofilms with QDs were scraped off from the plates and were placed into the 5 mL syringe barrels with a nozzle diameter of 160 μm. 3D structures were fabricated using a three-axis robotic deposition stage (GeSim BioScaffolder 3.1). The 3D shapes of polygons or circles were printed directly using the existing graph program in the system, other graphics or letters were printed using the imported stl program. The printing parameters applied in the experiments: printing pressure (150-250 kPa), the inner diameter of the nozzle (160 μm), and the printing speed (5-10 mm/s).

(3) Encapsulation of Printed Biofilms Inside Hydrogels Through Sequential Printing To evaluate the functionality and viability of printed biofilms in confined environments, we sequentially printed polymeric hydrogels and a strain that can produce a TasA-mCherry nanofibre biofilm using 3D printing technique.

Specifically, 5% (w/v) gelatin and 2% (w/v) sodium alginate was first dissolved in MSgg liquid and the viscous solution was then loaded in the barrels. The gelatin/alginate mixtures were first printed on PVC plate using a 3D printer (GeSim BioScaffolder 3.1), with the specific printing parameters described below: printing pressure (200-300 kPa), printing speed (5-10 mm/s), and the nozzle diameter (210 μm). The ΔtasAΔsinRΔeps/TasA-mCherry biofilms were scraped off from the culture plates and were placed into the charging barrels. Biofilms were directly printed on top of the printed gelatin/alginate hydrogel layers using the parameters below: printing pressure (150-250 kPa), printing speed (5-10 mm/s) and the nozzle diameter (160 μm). Afterwards, another hydrogel layer composed of 5% (w/v) gelatin and 2% (w/v) sodium alginate was printed directly on top of the printed biofilms to encapsulate the biofilms inside hydrogels.

To solidify the printed structures, the printed samples above were merged in 500 mM $CaCl_2$ until the sodium alginate hydrogels turned into white. The 3D hydrogels were then cultured in MSgg culture media and imaged with stereoscopic microscope Nikon SMZ25 for viability and functional performance evaluations.

12. Microencapsulated Biofilm Fabrication

To fabricate microencapsulated biofilms, a precursor solution consisting of mixed *B. subtilis* cells and sodium alginate was first prepared. Specifically, cells that express TasA-mCherry nanofibres were first cultured and harvested following the solid-plate biofilm culture protocol described above. The as-prepared biofilms were homogeneously mixed with 1.5% sodium alginate solution (1.5% low viscosity alginate in Morpholino propanesulfonic acid, MOPS washing-buffer). A 25-mL syringe loaded with 20 mL mixture attached to a reaction vessel was then connected to a control unit of the B-395 Pro encapsulator (BÜCHI Labortechnik AG, Flawil, Switzerland). Alginate micro-gel beads (400 μm diameters) were fabricated at a flow rate of 20 mL/min using a 200-μm nozzle, operated at vibration frequency of 1,300 Hz and voltage of 1.10 kV.

After 5-mM solidification in 500 mL of curing buffer (100 mM $CaCl_2$ and 10 mM MOPS), the micro-gel beads (10 mL) were then sequentially immersed in 75 mL of 0.05% Poly-L-Lysine (PLL) solution (0.05% w/v Poly-L-lysine (Mw=15,000~30,000) in MOPS washing buffer) and 75 mL of 0.03% w/v alginate solution (0.03% w/v low viscosity alginate in MOPS washing-buffer) to form two alternate-layer coated alginate beads, referred to as alginate-poly-(L-lysine)-alginate hydrogel microcapsules. The as-prepared microcapsules were then immersed in 75 mL of depolymerization solution (50 mM sodium citrate, 0.45% NaCl, 10 mM MOPS) for 5-10 mM to dissolve the core of the gels.

The fabricated microbeads were finally cultured in MSgg media supplemented with 0.5 mM IPTG inducer. Fluorescent imaging of the microbeads was performed using inverted fluorescence microscopy (Nikon ECLIPSE Ti). The size of the fabricated micro-gel beads is larger than 200 μm owing to swelling in solution.

13. Self-Regeneration Experiments

The TasA-HisTag biofilms grown on solid MSgg plate (supplemented with 5 μg/mL chloramphenicol and 0.5 mM IPTG) were scraped off and placed into the charging barrels of 3D printer. The biofilms were first printed into designed hexagonal patterns on glass slide. The edge length of the three printed hexagons was 5, 7 and 9 mm respectively. The 3D printed biofilms on the glass slide were then put upside down onto a new solid MSgg plate, and the biofilms could regrow in hexagonal patterns after 2 days. The biofilms re-growing in the hexagonal patterns on the first nutrient-rich agar plate were placed upside down on the second nutrient-rich agar plate. Similar regeneration experiments were repeated for another two rounds until biofilms re-growing in the hexagonal patterns on the third agar plate were put upside down on the fourth nutrient-agar plate.

14. Quantum Dots (QDs) Toxicity Assay

The biofilm-deficient strain (pHT01), TasA, and TasA-HisTag biofilm-producing strain were inoculated from frozen glycerol stocks and grown in LB medium using 5 μg/mL chloramphenicol. Seed cultures were grown for 12 h at 37° C. Static biofilm samples were grown at 30° C. in MSgg medium containing 5 μg/mL chloramphenicol and 0.5 mM IPTG, supplemented with or without 10% red Co-NTA CdSeS@ZnS QDs. After 2-day cultivation, biofilm production was measured using a standard crystal-violet (CV) assay for biofilm cultures (in the presence or absence of QDs) and influences of QDs on biofilm growth and production were assessed.

15. Long-Term Viability and Functional Performance Assessment for Trapped Biofilms in Hydrogels The printed hydrogels with trapped cells that express TasA-mCherry nanofibres and the microcapsules containing trapped cells that express TasA-mCherry nanofibres were produced following the protocols described above. To evaluate the functional performance of biofilms in confined environments, the samples were immersed into liquid MSgg medium supplemented with 5 μg/mL chloramphenicol and 0.5 mM IPTG. The sandwiched samples after different induction time were taken out for fluorescent detection. Fluorescent imaging was recorded using a stereoscopic microscope (Nikon SMZ25).

To evaluate the long-term viability and functional performance, the hydrogel structures were stored at 4° C. for more than 5 weeks and then immersed into liquid MSgg medium supplemented with 5 μg/mL chloramphenicol and 0.5 mM IPTG. The sandwiched samples were taken out for fluorescent detection. Fluorescent imaging was recorded using a stereoscopic microscope (Nikon SMZ25). Hydrogels immersed in media without IPTG were used as control samples.

Supplementary Table 1 Genes involved in biofilms matrix

| Gene or operon | Role of encoded proteins in matrix production |
|---|---|
| eps operon | Produces exopolysaccharide |
| tasA | Major protein component of TasAfibres |
| tapA | Anchor TasAfibres to the cell |
| sipW | Signal peptidase required for TapA and TasA processing and secretion |
| bslA | Provides surface hydrophobicity |
| pgsB | Produces γ-poly-dl-glutamic acid (together with several other pgsoperon enzymes) |

Supplementary Table 2 Strains and plasmids

| Strains | Description and phenotype |
|---|---|
| 2569 | Wild-type *Bacillus subtilis* producing biofilm, ancestral 3610 strain with competence |
| ΔtasAΔsinR | tasA and sinR deletions |
| ΔtasAΔsinR Δeps | epsA-O gene cluster deletion, tasA deletion, and sinR deletion |
| Plasmids | |
| pHT01 | Shuttle expression plasmid in *E. coli* and *B. subtilis*, Pgrac promoter (IPTG induction), AmpR in *E. coli*, CmR in *B. subtilis* |
| pHT-tasA | Wild-type tasA from 2569 under control of Pgrac promoter, CmR |
| pHT-tasA-histag | tasA-histag expression plasmid under control of Pgrac, CmR |
| pHT-tasA-spytag | tasA-spytag expression plasmid under control of Pgrac, CmR |
| pHT-tasA-mefp3 | tasA-mefp3 expression plasmid under control of Pgrac, CmR |
| pHT-tasA-mefp5 | tasA-mefp5 expression plasmid under control of Pgrac, CmR |
| pHT-tasA-mms6 | tasA-mms6 expression plasmid under control of Pgrac, CmR |
| pHT-tasA-mcherry | tasA-mcherry expression plasmid under control of Pgrac, CmR |
| pHT-tasA-oph | tasA-oph expression plasmid under control of Pgrac, CmR |
| pHT-tasA-petase | tasA-petase expression plasmid under control of Pgrac, CmR |
| pHT-tasA-mhetase | tasA-mhetase expression plasmid under control of Pgrac, CmR |

Supplementary Table 3 Primers

| Primers | Primer sequence (listed 5' to 3') | note |
|---|---|---|
| sal-dAF | GGGGTCGACATGTTTCGATTGTTTCAC AATCAG (SEQ ID NO: 03) | For tasAsinR deletion |
| dcAR | TCATACCGTAAATCCTTTCTGATTAAG TAGACATGGTGCTGTC (SEQ ID NO: 04) | For tasAsinR deletion |
| daCF | GACAGCACCATGTCTACTTAATCAGAA AGGATTTACGGTATGA (SEQ ID NO: 05) | For tasAsinR deletion |
| bgl-dCR | GCGAGATCTGCGTTTTTTTCAAGCAAA CAG (SEQ ID NO: 06) | For tasAsinR deletion |
| Bam-d EPS A up F | AAAGGATCCGCAATCCTCGGACTGGC GGG (SEQ ID NO: 07) | For epsA-O cluster deletion |
| d EPS A up R | GAGAATCAAAATAAACCTTCCGCGTAT TCATAGCCTTCAGCCTTCC (SEQ ID NO: 08) | For epsA-O cluster deletion |
| d EPS O dw F | GGAAGGCTGAAGGCTATGAATACGCG GAAGGTTTATTTTGATTCTC (SEQ ID NO: 09) | For epsA-O cluster deletion |
| Sal-d EPS O dw R | AAAGTCGACTTCCGCTGCGATGTGCCC AT (SEQ ID NO: 10) | For epsA-O cluster deletion |
| Bam-tasAF | GGGGGATCCATGGGTATGAAAAAGAA ATTGAGTTTAGGA (SEQ ID NO: 11) | For pHT-tasA |
| Sma-tasAR | GGGCCCGGGTTAATTTTTATCCTCGCT ATGCGCTTTTTC (SEQ ID NO: 12) | For pHT-tasA |
| Sma-tasAHisR | GGGCCCGGGTTAGTGGTGGTGGTGGTG GTGATTTTTATC (SEQ ID NO: 13) | For pHT-tasA-H6 |
| Sma-tasA-spytag R | GGGCCCGGGTTATTTGGTGGGTTTATA TGCATCGACCATAACGATGTGCGCGGA GCCCCCGCCGGAGCCCCCGCCATTTTT ATCCTCGCTATG (SEQ ID NO: 14) | For pHT-tasA-spytag |
| tasA(01)-GA F | TCTTTATTATAAGAATTGTGGAATTGT GAGCGGATAACAATTCCCAATTAAAG | Forward primer for tasA-R fusion into pHT01 by Gibson |

-continued

Supplementary Table 3
Primers

| Primers | Primer sequence (listed 5' to 3') | note |
|---|---|---|
| | GAGGAAGATGGGTATGAAAAAGAAAT TGAGTT (SEQ ID NO: 15) | Assembly |
| TasA(mefp3)-GA R | TTCGGGCCATAGTAATCCGCGGATCCT GAGCCTCCTCCTCCTGATCCTCCGCCG CCGCCGGCATTTTTATCCTCGCTATGC GCTTTT (SEQ ID NO: 16) | Reverse primer for tasA fused with mefp3 |
| Mefp3(tasA)-GA F | AAAAGCGCATAGCGAGGATAAAAATG CCGGCGGCGGCGGAGGATCAGGAGGA GGAGGCTCAGGATCCGCGGATTACTAT GGCCCGAA (SEQ ID NO: 17) | Forward primer for Mefp3 fused with tasA |
| Mefp3(01)-GA R | TGAAAAAAGCCCGCTCATTAGGCGGG CTGCCCCGGGGACGTCGACTCTAGAGG ATCTTATGGCCAATGATGATGGTGATG ATGGTGACTAGTCCAGTATTTGCCGCG TCTGC (SEQ ID NO: 18) | Reverse primer for tasA-mefp3 fused into pHT01 |
| TasA(mefp5)-GA R | CGCCCTTATACTCTTCGCTGCTGGATC CTGAGCCTCCTCCTCCTGATCCTCCGC CGCCGCCGGCATTTTTATCCTCGCTAT GCGCTTTT (SEQ ID NO: 19) | Reverse primer for tasA fused with mefp5 |
| Mefp5(tasA)-GA F | AAAAGCGCATAGCGAGGATAAAAATG CCGGCGGCGGCGGAGGATCAGGAGGA GGAGGCTCAGGATCCAGCAGCGAAGA GTATAAGGGCG (SEQ ID NO: 20) | Forward primer for Mefp5 fused with tasA |
| Mefp5(01)-GA R | TGAAAAAAGCCCGCTCATTAGGCGGG CTGCCCCGGGGACGTCGACTCTAGAGG ATCTTATGGCCAATGATGATGGTGATG ATGGTGACTAGTGCTGCTGCCGCCGTA ATACTTA (SEQ ID NO: 21) | Reverse primer for tasA-mefp5 fused into pHT01 |
| tasA(mms) R | TCCAAATTGTGCCGCCGCTGCCGCCGC CGCCTGATCCTCCGCCGCCATTTTTATC CTCGCTATGCGCTTTTTCATTTTCTTTC ACG (SEQ ID NO: 22) | Reverse primer for tasA fused with mms6 |
| mms (tasA) F | CGTGAAAGAAAATGAAAAAGCGCATA GCGAGGATAAAAATGGCGGCGGAGGA TCAGGCGGCGGCGGCAGCGGCGGCAC AATTTGGA (SEQ ID NO: 23) | Forward primer for Mms6 fused with tasA |
| mms(01) R | CGCTCATTAGGCGGGCTGCCCCGGGGA CGTCGACTCTAGAGGATCTTAATGATG ATGGTGATGATGGTGTGCCAGCGCATC GCGCAGTTC (SEQ ID NO: 24) | Reverse primer for tasA-mms6 fused into pHT01 |
| TasA(cherry)-GA R | GTGAGCAAGGGCGAGGAGGAGGATCC TGAGCCTCCTCCTCCTGATCCTCCGCC GCCGCCGGCATTTTTATCCTCGCTATG CGCTTTT (SEQ ID NO: 25) | Reverse primer for tasA fused with mcherry |
| cherry(tasA)-GA F | AAAAGCGCATAGCGAGGATAAAAATG CCGGCGGCGGCGGAGGATCAGGAGGA GGAGGCTCAGGATCCGTGAGCAAGGG CGAGGAGGA (SEQ ID NO: 26) | Forward primer for mcherry fused with tasA |
| cherry(01)-GA R | TGAAAAAAGCCCGCTCATTAGGCGGG CTGCCCCGGGGACGTCGACTCTAGAGG ATCTTAATGATGATGGTGATGATGGTG ACTAGTACCCGCCTTGTACAGCTCGTC (SEQ ID NO: 27) | Reverse primer for tasA-mcherry fused into pHT01 |
| tasA(OPH)-GA R | CCGCCTGATCCTCCGCCGCCGCCGGCA TTTTTATCCTCGCTATGCGC (SEQ ID NO: 28) | Reverse primer for tasA fused with oph |
| OPH (tasA)F | CGTGAAAGAAAATGAAAAAGCGC (SEQ ID NO: 29) | Forward primer for oph fused with tasA |
| OPH R(tasA)R | TGAAAAAAGCCCGCTCATTAGG (SEQ ID NO: 30) | Reverse primer for tasA-oph fused into pHT01 |

-continued

Supplementary Table 3
Primers

| Primers | Primer sequence (listed 5' to 3') | note |
|---|---|---|
| Bam-OPH no his F | TCAGGATCCTCTATCGGTACCGGT (SEQ ID NO: 31) | Forward primer for oph fused with vector pHT-tasA |
| Xba-OPH no his R | GACTCTAGAGGATCTTAACTAGTTGAC GCCCGCAAGGTCGGTG (SEQ ID NO: 32) | Reverse primer for oph fused with vector pHT-tasA |

Supplementary Table 4
Sequences

| Gene name | Part Type | Gene sequence |
|---|---|---|
| tas A | Gene coded for Amyloid-like protein | ATGGGTATGAAAAAGAAATTGAGTTTAGGAGTTGCTTCTG<br>CAGCACTAGGATTAGCTTTAGTTGGAGGAGGAACATGGGC<br>AGCATTTAACGACATTAAATCAAAGGATGCTACTTTTGCA<br>TCAGGTACGCTTGATTTATCTGCTAAAGAGAATTCAGCGA<br>GTGTGAACTTATCAAATCTAAAGCCGGGAGATAAGTTGAC<br>AAAGGATTTCCAATTTGAAAATAACGGATCACTTGCGATC<br>AAAGAAGTTCTAATGGCGCTTAATTATGGAGATTTTAAAG<br>CAAACGGCGGCAGCAATACATCTCCAGAAGATTTCCTCAG<br>CCAGTTTGAAGTGACATTGTTGACAGTTGGAAAAGAGGGC<br>GGCAATGGCTACCCGAAAAACATTATTTTAGATGATGCGA<br>ACCTTAAAGACTTGTATTTGATGTCTGCTAAAAATGATGC<br>AGCGGCTGCTGAAAAAATCAAAAAACAAATTGACCCTAA<br>ATTCTTAAATGCAAGCGGTAAAGTCAATGTAGCAACAATT<br>GATGGTAAAACCGCTCCTGAATATGATGGTGTTCCAAAAA<br>CACCAACTGACTTCGATCAGGTTCAAATGGAAATCCAATT<br>CAAGGATGATAAAACAAAAGATGAAAAAGGGCTTATGGT<br>TCAAAATAAATATCAAGGCAACTCCATTAAGCTTCAATTC<br>TCATTCGAAGCTACACAGTGGAACGGCTTGACAATCAAAA<br>AGGACCATACTGATAAAGATGGTTACGTGAAAGAAAATG<br>AAAAAGCGCATAGCGAGGATAAAAAT (SEQ ID NO: 33) |
| histag | an affinity tag | CACCACCACCACCACCAC (SEQ ID NO: 34) |
| spytag | a short peptide | GCGCACATCGTTATGGTCGATGCATATAAACCCACCAAA<br>(SEQ ID NO: 35) |
| gfp-spycatcher | Gene encoding the fusion protein GFP-spycatcher | ATGGTGAGCAAGGGCGAGGAGCTGTTCACCGGGGTGGTG<br>CCCATCCTGGTCGAGCTGGACGGCGACGTAAACGGCCACA<br>AGTTCAGCGTGTCCGGCGAGGGCGAGGGCGATGCCACCTA<br>CGGCAAGCTGACCCTGAAGTTCATCTGCACCACCGGCAAG<br>CTGCCCGTGCCCTGGCCCACCCTCGTGACCACCCTGACCTA<br>CGGCGTGCAGTGCTTCAGCCGCTACCCCGACCACATGAAG<br>CAGCACGACTTCTTCAAGTCCGCCATGCCCGAAGGCTACG<br>TCCAGGAGCGCACCATCTTCTTCAAGGACGACGGCAACTA<br>CAAGACCCGCGCCGAGGTGAAGTTCGAGGGCGACACCCT<br>GGTGAACCGCATCGAGCTGAAGGGCATCGACTTCAAGGA<br>GGACGGCAACATCCTGGGGCACAAGCTGGAGTACAACTA<br>CAACAGCCACAACGTCTATATCATGGCCGACAAGCAGAAG<br>AACGGCATCAAGGTGAACTTCAAGATCCGCCACAACATCG<br>AGGACGGCAGCGTGCAGCTCGCCGACCACTACCAGCAGA<br>ACACCCCCATCGGCGACGGCCCCGTGCTGCTGCCCGACAA<br>CCACTACCTGAGCACCCAGTCCAAACTGAGCAAAGACCCC<br>AACGAGAAGCGCGATCACATGGTCCTGCTGGAGTTCGTGA<br>CCGCCGCCGGGATCACTCTCGGCATGGACGAGCTGTACAA<br>GGCGGGTGGCGGTGGTGGTAGCGGTGGTGGCGGTAGCTCG<br>TACTACCATCACCATCACCATCACGATTACGACATCCCAA<br>CGACCGAAAACCTGTATTTTCAGGGCGCCATGGTAACCAC<br>CTTATCAGGTTTATCAGGTGAGCAAGGTCCGTCCGGTGAT<br>ATGACAACTGAAGAAGATAGTGCTACCCATATTAAATTCT<br>CAAAACGTGATGAGGACGGCCGTGAGTTAGCTGGTGCAAC<br>TATGGAGTTGCGTGATTCATCTGGTAAAACTATTAGTACAT<br>GGATTTCAGATGGACATGTGAAGGATTTCTACCTGTATCC<br>AGGAAAATATACATTTGTCGAAACCGCAGCACCAGACGGT<br>TATGAGGTAGCAACTGCTATTACCTTTACAGTTAATGAGC<br>AAGGTCAGGTTACTGTAAATGGCGAAGCAACTAAAGGTG<br>ACGCTCATACTTAA (SEQ ID NO: 36) |

-continued

Supplementary Table 4
Sequences

| Gene name | Part Type | Gene sequence |
|---|---|---|
| mms6 | peptide for magnetite templating | GGCGGCACAATTTGGACAGGCAAAGGCCTTGGCCTGGGCC TGGGACTTGGACTTGGCGCATGGGGCCCGATTATTCTGGG CGTTGTGGGCGCAGGCGCAGTGTATGCGTACATGAAAAGC CGCGACATCGAATCAGCGCATAGCGACGAAGAAGTGGAA CTGCGCGATGCGCTGGCA (SEQ ID NO: 37) |
| mefp3 | Mussel foot protein 3 | GCGGATTACTATGGCCCGAATTATGGACCGCCGCGCCGCT ATGGAGGCGGCAATTACAACCGCTATAACCGCTATGGCCG CCGCTATGGCGGCTATAAGGGCTGGAATAACGGCTGGAAT CGCGGCAGACGCGGCAAATACTGG (SEQ ID NO: 38) |
| mefp5 | Mussel foot protein 5 | AGCAGCGAAGAGTATAAGGGCGGCTATTATCCTGGTAATG CGTATCACTACCATTCAGGCGGCAGCTATCATGGCTCAGG CTATCATGGCGGCTATAAGGGCAAATACTACGGCAAGGCG AAAAAATATTATTATAAATATAAAAATAGCGGCAAGTATA AATATCTGAAAAAAGCGCGCAAATACCATCGCAAGGGCT ATAAGTATTACGGCGGCAGCAGC (SEQ ID NO: 39) |
| mcherry | Fluorescentre porter protein | ATGGTGAGCAAGGGCGAGGAGGATAACATGGCCATCATC AAGGAGTTCATGCGCTTCAAGGTGCACATGGAGGGCTCCG TGAACGGCCACGAGTTCGAGATCGAGGGCGAGGGCGAGG GCCGCCCCTACGAGGGCACCCAGACCGCCAAGCTGAAGGT GACCAAGGGTGGCCCCCTGCCCTTCGCCTGGGACATCCTG TCCCCTCAGTTCATGTACGGCTCCAAGGCCTACGTGAAGC ACCCCGCCGACATCCCCGACTACTTGAAGCTGTCCTTCCCC GAGGGCTTCAAGTGGGAGCGCGTGATGAACTTCGAGGAC GGCGGCGTGGTGACCGTGACCCAGGACTCCTCCCTGCAGG ACGGCGAGTTCATCTACAAGGTGAAGCTGCGCGGCACCAA CTTCCCCTCCGACGGCCCCGTAATGCAGAAGAAGACGATG GGCTGGGAGGCCTCCTCCGAGCGGATGTACCCCGAGGACG GCGCCCTGAAGGGCGAGATCAAGCAGAGGCTGAAGCTGA AGGACGGCGGCCACTACGACGCTGAGGTCAAGACCACCT ACAAGGCCAAGAAGCCCGTGCAGCTGCCCGGCGCCTACA ACGTCAACATCAAGTTGGACATCACCTCCCACAACGAGGA CTACACCATCGTGGAACAGTACGAACGCGCCGAGGGCCGC CACTCCACCGGCGGCATGGACGAGCTGTACAAGGCGGGT (SEQ ID NO: 40) |
| oph | organophosp horns hydrolase | ATGTCAATTGGCACGGGCGATCGCATCAACACAGTGAGAG GCCCGATCACAATTAGCGAAGCGGGCTTTACACTGACGCA TGAGCATATCTGCGGCAGCTCAGCGGGCTTTCTTCGCGCA TGGCCGGAATTTTTTGGCAGCCGCAAAGCGCTGGCAGAAA AAGCGGTGAGAGGCCTGAGAAGAGCGAGAGCAGCGGGCG TTCGCACGATTGTGGATGTGAGCACGTTTGACATCGGCAG AGATGTGAGCCTGCTGGCGGAAGTTAGCCGCGCAGCAGAT GTGCATATCGTGGCAGCGACGGGACTGTGGTTTGATCCGC CTCTTAGCATGCGCCTTCGCAGCGTGGAGGAACTGACGCA GTTTTTCCTGCGCGAAATCCAGTACGGCATCGAAGATACG GGCATTAGAGCGGGCATCATCAAAGTGGCGACAACGGGA AAGGCAACACCGTTTCAGGAGCTGGTTCTGAAAGCAGCAG CAAGAGCATCACTGGCGACAGGCGTGCCGGTTACGACACA TACAGCAGCGTCACAGCGCGATGGCGAACAACAGGCGGC GATCTTCGAATCAGAAGGCCTGTCACCTTCACGCGTGTGT ATCGGCCATAGCGATGATACGGACGATCTGAGCTACCTGA CAGCACTGGCGGCACGCGGCTATCTGATTGGCCTGGACCA TATCCCGCACTCAGCAATCGGCCTGGAAGATAATGCGAGC GCAAGCGCGCTGCTGGGCATTAGAAGCTGGCAGACGAGA GCGCTTCTGATCAAGGCGCTGATCGATCAGGGCTACATGA AGCAGATTCTGGTGAGCAACGACTGGCTGTTTGGCTTCAG CAGCTATGTGACGAACATTATGGACGTGATGGATCGCGTG AATCCGGATGGCATGGCATTTATCCCGCTGAGAGTGATCC CGTTTCTTCGCGAAAAAGGCGTGCCGCAGGAAACACTGGC AGGCATCACGGTGACAAATCCGGCGAGATTTCTGAGCCCG ACACTGAGAGCGAGC (SEQ ID NO: 41) |
| maple 3 | Fluorescentre porter protein | ATGGTGAGCAAAGGCGAGGAGACAATCATGTCCGTGATC AAGCCCGACATGAAGATCAAACTGAGGATGGAGGGCAAC GTGAACGGCCACGCCTTCGTGATCGAGGGCGAAGGAAGC GGCAAGCCCTTCGAGGGCATCCAGACCATCGATCTGGAGG TCAAGGAGGGCGCTCCCCTCCCTTTCGCCTATGACATCCTG ACCACCGCCTTCCACTACGGCAATAGGGTGTTCACCAAGT ATCCCAGGAAGATCCCCGACTACTTCAAGCAGAGCTTCCC TGAGGGCTACAGCTGGGAGAGGAGCATGACATACGAGGA |

-continued

Supplementary Table 4
Sequences

| Gene name | Part Type | Gene sequence |
|---|---|---|
| | | CGGCGGCATCTGCAACGCCACCAACGACATCACAATGGAG GAGGACAGCTTCATCAACAAGATCCACTTCAAAGGCACAA ACTTCCCCCCCAATGGCCCCGTGATGCAGAAGAGGACCGT GGGCTGGGAGGTGAGCACCGAGAAGATGTACGTGAGGGA CGGCGTCCTGAAGGGCGACGTGAAGATGAAGCTCCTGCTC AAGGGCGGCAGCCACTACAGGTGCGACTTTAGGACCACCT ATAAGGTGAAGCAGAAGGCTGTGAAGCTGCCCAAGGCCC ACTTCGTCGACCATAGGATCGAGATCCTGTCCCACGACAA GGACTACAACAAGGTCAAGCTGTACGAGCACGCCGTCGCT AGGAACAGCACCGACAGCATGGACGAACTCTATAAG (SEQ ID NO: 42) |
| petase | poly(ethylene terephthalate) hydrolase | ATGAACTTTCCGAGAGCGAGCAGACTGATGCAAGCGGCA GTGCTTGGAGGCCTTATGGCGGTTTCAGCGGCGGCAACAG CGCAGACAAATCCGTATGCGAGAGGACCGAATCCGACGG CAGCGTCACTTGAAGCGAGCGCTGGTCCGTTTACAGTTCG CAGCTTCACAGTGAGCAGACCGTCTGGTTATGGCGCTGGT ACGGTGTATTATCCGACAAATGCTGGTGGCACGGTTGGAG CAATTGCGATTGTGCCGGGCTACACAGCGCGCCAAAGCAG CATTAAATGGTGGGGCCCTAGACTGGCAAGCCACGGCTTT GTGGTGATCACGATTGACACGAACAGCACACTGGACCAGC CGAGCTCAAGAAGCAGCCAACAAATGGCGGCACTGCGCC AAGTTGCATCTTTAAATGGCACGTCAAGCAGCCCGATCTA TGGCAAAGTGGATACGGCGCGCATGGGAGTGATGGGATG GTCAATGGGAGGCGGAGGCTCACTGATCAGCGCGGCAAA TAACCCGTCTTTAAAAGCGGCAGCACCGCAAGCGCCTTGG GATAGCAGCACAAACTTCAGCAGCGTTACGGTGCCGACAC TGATCTTTGCGTGCGAGAACGATAGCATCGCGCCGGTTAA TTCTAGCGCGCTGCCGATTTACGACAGCATGTCACGCAAC GCGAAACAATTTTTAGAGATCAACGGCGGCAGCCATTCAT GCGCGAACAGCGGCAATAGCAACCAAGCTCTGATCGGCA AAAAAGGAGTGGCATGGATGAAGCGCTTCATGGATAACG ACACGCGCTACAGCACATTCGCGTGCGAAAACCCGAACAG CACGAGAGTGAGCGATTTTCGCACGGCGAATTGCTCA (SEQ ID NO: 43) |
| mhetase | Mono-(2-hydroxyethyl) terephthalate hydrolase | ATGCAGACAACAGTGACGACAATGCTGCTGGCATCAGTGG CGCTTGCAGCATGTGCTGGTGGAGGCTCAACACCGCTGCC GCTTCCGCAGCAACAACCGCCTCAACAAGAACCTCCGCCG CCGCCCGTTCCGCTTGCGTCAAGAGCAGCGTGCGAAGCGC TTAAAGATGGCAATGGCGACATGGTGTGGCCGAATGCAGC AACAGTGGTTGAAGTGGCGGCATGGAGAGATGCAGCACC CGCTACAGCAAGCGCAGCGGCACTTCCGGAACATTGCGAA GTGTCTGGTGCGATTGCGAAACGCACGGGAATTGATGGCT ACCCGTACGAGATCAAATTTCGCCTTCGCATGCCGGCAGA GTGGAATGGCCGCTTTTTCATGGAAGGCGGAAGCGGAACG AATGGCTCACTTTCAGCGGCAACTGGTAGCATCGGCGGAG GCCAGATTGCAAGCGCACTGAGCCGCAATTTTGCGACAAT CGCAACGGACGGCGGCCATGATAATGCGGTGAACGATAA CCCGGACGCACTGGGCACAGTGGCATTCGGCCTTGATCCG CAAGCTAGACTGGACATGGGCTATAACAGCTACGATCAAG TTACGCAAGCGGGCAAAGCAGCGGTGGCGAGATTTTACGG CAGAGCGGCGGACAAAAGCTACTTTATCGGATGCTCAGAG GGCGGCAGAGAAGGCATGATGCTGTCACAGCGCTTTCCGT CACACTATGATGGCATCGTTGCGGGCGCACCGGGATATCA GCTGCCGAAAGCGGGCATTTCTGGTGCATGGACGACACAA AGCCTTGCGCCCGCTGCTGTTGGCCTTGACGCGCAAGGTG TTCCGCTGATCAACAAGAGCTTTAGCGACGCGGATCTTCA CCTTCTGAGCCAAGCGATTCTGGGAACATGCGATGCGCTG GATGGTTTAGCGGATGGCATTGTTGACAACTACAGAGCGT GCCAAGCTGCGTTTGACCCGGCGACAGCAGCAAACCCGGC AAATGGCCAAGCTTTACAATGCGTGGGCGCAAAAACAGC GGATTGTTTAAGCCCGGTTCAAGTTACGGCGATCAAGCGC GCAATGGCTGGTCCGGTGAACAGCGCTGGTACACCGCTGT ATAACAGATGGGCATGGGATGCTGGTATGAGCGGTTTAAG CGGCACAACGTACAACCAAGGTTGGCGCTCATGGTGGCTT GGCAGCTTCAATTCAAGCGCGAACAACGCGCAGAGAGTTA GCGGCTTTTCAGCGAGAAGCTGGCTGGTGGATTTCGCGAC ACCGCCGGAACCGATGCCGATGACACAAGTTGCGGCAAG AATGATGAAGTTCGACTTCGACATCGATCCGCTGAAAATC TGGGCGACAAGCGGCCAGTTTACGCAGTCAAGCATGGATT GGCACGGAGCGACAAGCACAGATCTGGCGGCATTTCGCG ATCGCGGCGGCAAGATGATTCTGTACCATGGAATGAGCGA |

-continued

Supplementary Table 4
Sequences

| Gene name | Part Type | Gene sequence |
|---|---|---|
| | | CGCGGCGTTTAGCGCGCTGGATACGGCGGACTACTATGAG CGCCTTGGAGCAGCAATGCCGGGAGCAGCTGGTTTTGCAC GCCTTTTCCTTGTGCCGGGCATGAACCATTGCAGCGGCGG ACCGGGAACAGATCGCTTCGACATGCTTACACCGCTGGTG GCATGGGTTGAAAGAGGCGAAGCGCCGGATCAGATCAGC GCATGGAGCGGCACACCGGGCTATTTTGGAGTGGCAGCAA GAACGAGACCGCTGTGTCCGTATCCGCAGATCGCGCGCTA CAAAGGAAGCGGCGATATCAACACAGAAGCGAATTTTGC ATGCGCGGCACCGCCT (SEQ ID NO: 44) |

Supplementary Table 5
Amino acid sequences

| Name | Amino acids sequence | Length |
|---|---|---|
| TasA | MGMKKKLSLGVASAALGLALVGGGTWAAFNDIKSKDATFASGT LDLSAKENSASVNLSNLKPGDKLTKDFQFENNGSLAIKEVLMAL NYGDFKANGGSNTSPEDFLSQFEVTLLTVGKEGGNGYPKNIILDD ANLKDLYLMSAKNDAAAAEKIKKQIDPKFLNASGKVNVATIDGK TAPEYDGVPKTPTDFDQVQMEIQFKDDKTKDEKGLMVQNKYQG NSIKLQFSFEATQWNGLTIKKDHTDKDGYVKENEKAHSEDKN (SEQ ID NO: 45) | 261 aa |
| His | HHHHHH (SEQ ID NO: 46) | 6 aa |
| Spytag | AHIVMVDAYKPTK (SEQ ID NO: 47) | 13 aa |
| Mms6 | GGTIWTGKGLGLGLGLGLGAWGPIILGVVGAGAVYAYMKSRDIE SAHSDEEVELRDALA (SEQ ID NO: 48) | 59 aa |
| Mefp3 | ADYYGPNYGPPRRYGGGNYNRYNRYGRRYGGYKGWNNGWNR GRRGKYW (SEQ ID NO: 49) | 48 aa |
| Mefp5 | SSEEYKGGYYPGNAYHYHSGGSYHGSGYHGGYKGKYYGKAKK YYYKYKNSGKYKYLKKARKYHRKGYKYYGGSS (SEQ ID NO: 50) | 74 aa |
| mCherry | VSKGEEDNMAIIKEFMRFKVHMEGSVNGHEFEIEGEGEGRPYEG TQTAKLKVTKGGPLPFAWDILSPQFMYGSKAYVKHPADIPDYLK LSFPEGFKWERVMNFEDGGVVTVTQDSSLQDGEFIYKVKLRGTN FPSDGPVMQKKTMGWEASSERMYPEDGALKGEIKQRLKLKDGG HYDAEVKTTYKAKKPVQLPGAYNVNIKLDITSHNEDYTIVEQYE RAEGRHSTGGMDELYKAG (SEQ ID NO: 51) | 237 aa |
| OPH | MSIGTGDRINTVRGPITISEAGFTLTHEHICGSSAGFLRAWPEFFGS RKALAEKAVRGLRRARAAGVRTIVDVSTFDIGRDVSLLAEVSRA ADVHIVAATGLWFDPPLSMRLRSVEELTQFFLREIQYGIEDTGIRA GIIKVATTGKATPFQELVLKAAARASLATGVPVTTHTAASQRDGE QQAAIFESEGLSPSRVCIGHSDDTDDLSYLTALAARGYLIGLDHIP HSAIGLEDNASASALLGIRSWQTRALLIKALIDQGYMKQILVSND WLFGFSSYVTNIMDVMDRVNPDGMAFIPLRVIPFLREKGVPQETL AGITVTNPARFLSPTLRAS (SEQ ID NO: 52) | 337 aa |
| Maple3 | MVSKGEETIMSVIKPDMKIKLRMEGNVNGHAFVIEGEGSGKPFE GIQTIDLEVKEGAPLPFAYDILTTAFHYGNRVFTKYPRKIPDYFKQ SFPEGYSWERSMTYEDGGICNATNDITMEEDSFINKIHFKGTNFPP NGPVMQKRTVGWEVSTEKMYVRDGVLKGDVKMKLLLKGGSH YRCDFRTTYKVKQKAVKLPKAHFVDHRIEILSHDKDYNKVKLYE HAVARNSTDSMDELYK (SEQ ID NO: 53) | 237 aa |
| PETase | MNFPRASRLMQAAVLGGLMAVSAAATAQTNPYARGPNPTAASL EASAGPFTVRSFTVSRPSGYGAGTVYYPTNAGGTVGAIAIVPGYT ARQSSIKWWGPRLASHGFVVITIDTNSTLDQPSSRSSQQMAALRQ VASLNGTSSSPIYGKVDTARMGVMGWSMGGGGSLISAANNPSLK AAAPQAPWDSSTNFSSVTVPTLIFACENDSIAPVNSSALPIYDSMS RNAKQFLEINGGSHSCANSGNSNQALIGKKGVAWMKRFMDNDT RYSTFACENPNSTRVSDFRTANCS (SEQ ID NO: 54) | 290 aa |
| MHETase | MQTTVTTMLLASVALAACAGGGSTPLPLPQQQPPQQEPPPPPVPL ASRAACEALKDGNGDMVWPNAATVVEVAAWRDAAPATASAA ALPEHCEVSGAIAKRTGIDGYPYEIKFRLRMPAEWNGRFFMEGGS | 603 aa |

-continued

Supplementary Table 5
Amino acid sequences

| Name | Amino acids sequence | Length |
|---|---|---|
| | GTNGSLSAATGSIGGGQIASALSRNFATIATDGGHDNAVNDNPDA LGTVAFGLDPQARLDMGYNSYDQVTQAGKAAVARFYGRAADK SYFIGCSEGGREGMMLSQRFPSHYDGIVAGAPGYQLPKAGISGA WTTQSLAPAAVGLDAQGVPLINKSFSDADLHLLSQAILGTCDAL DGLADGIVDNYRACQAAFDPATAANPANGQALQCVGAKTADCL SPVQVTAIKRAMAGPVNSAGTPLYNRWAWDAGMSGLSGTTYN QGWRSWWLGSFNSSANNAQRVSGFSARSWLVDFATPPEPMPMT QVAARMMKFDFDIDPLKIWATSGQFTQSSMDWHGATSTDLAAF RDRGGKMILYHGMSDAAFSALDTADYYERLGAAMPGAAGFARL FLVPGMNHCSGGPGTDRPDMLTPLVAWVERGEAPDQISAWSGTP GYFGVAARTRPLCPYPQIARYKGSGDINTEANFACAAPP (SEQ ID NO: 55) | |

REFERENCES FOR SUPPLEMENTARY MATERIALS

1. Arnaud, M., Chastanet, A. & Debarbouille, M. New vector for efficient allelic replacement in naturally non-transformable, low-GC-content, gram-positive bacteria. Applied and environmental microbiology70, 6887-6891 (2004).
2. Branda, et al. A major protein component of the *Bacillus subtilis* biofilm matrix. Molecular microbiology59, 1229-1238 (2006).
3. Chen, A. Y. et al. Synthesis and patterning of tunable multiscale materials with engineered cells. Nat Mater13, 515-523 (2014).
4. Vlamakis, H., Chai, Y., Beauregard, P., Losick, R. & Kolter, R. Sticking together: building a biofilm the *Bacillus subtilis* way. Nature reviews. Microbiology11, 157-168 (2013).

The invention claimed is:

1. A three-dimensional, living, self-regenerative structure of predetermined geometry comprising a solidified print material comprising a biofilm of engineered *Bacillus subtilis* comprising a TasA-R protein, wherein TasA is the major biofilm matrix component protein of *Bacillus subtilis*, and R is a recombinant, heterologous functional peptide or protein or enzyme, wherein the TasA-R is secreted and self-assembled into an extracellular nano-architecture with a tunable physiochemical property as a function of the R group.

2. The structure of claim 1, wherein the TasA-R protein is inducibly expressed.

3. The structure of claim 1, wherein the TasA-R protein is inducibly expressed, and the *Bacillus subtilis* lacks functional sinR and epsA~O genes.

4. The structure of claim 1, wherein the biofilm comprises first and second *Bacillus subtilis*, engineered with first and second TasA-R proteins, providing different first and second physiochemical properties, respectively.

5. The structure of claim 1, wherein the biofilm comprises first and second *Bacillus subtilis*, engineered with first and second TasA-R proteins, providing different first and second physiochemical properties, respectively, wherein the biofilm provides a two-step catalytic cascade comprising organophosphate hydrolase (OPH)-catalyzed degradation of paraoxon (PAR) into paranitrophenol (PNP), and a reaction catalyzed by HisTag-immobilized gold NPs (AuNPs) in which the PNP is further degraded into p-aminophenol (PAP).

6. The structure of claim 1, further comprising quantum dots (QDs) immobilized in the extracellular nano-architecture.

7. The structure of claim 1, further comprising quantum dots (QDs) immobilized in the extracellular nano-architecture, wherein the immobilization protects the *Bacillus subtilis* from direct damage from the quantum dots which are otherwise toxic to the *Bacillus subtilis.*

8. The structure of claim 1, further comprising quantum dots (QDs) immobilized in the extracellular nano-architecture, wherein the quantum dots are blue (CdZnS/ZnS core/shell), red (CdSeS/ZnS core/shell), or green (CdZnSeS/ZnS core/shell).

9. The structure of claim 1, wherein further gold nanoparticles are immobilized in the extracellular nano-architecture.

10. A structure comprising first and second structures according to claim 1, wherein the second structure is a regenerated clone of the first structure.

11. The structure of claim 1, wherein the R group comprising the peptide is selected from HisTag and SpyTag.

12. The structure of claim 1, wherein the R group comprising the protein is selected from Mefp3, Mms6 and Mefp5.

13. The structure of claim 1, wherein the R group comprising the protein is a fluorescent protein.

14. The structure of claim 13, wherein the enzyme is selected from Maple and mCherry.

15. The structure of claim 1, wherein the R group comprises the enzyme.

16. The structure of claim 1, wherein the enzyme is selected from PETase (polyethylene terephthalate esterase), OPH (organophosphorus hydrolase), and MHETase (mono-(2-hydroxvethyl)terechthalic acid hydrolase).

17. The structure of claim 1 wherein the geometry is at a resolution of resolution of 50-250 um.

18. The structure of claim 1 wherein the structure further encapsulated in a hydrogel or a microgel.

19. A method of making the structure of claim 1 comprising printing the structure.

20. A method of replicating the structure of claim 1 comprising contacting the structure with a matrix comprising a growth medium wherein the *Bacillus subtilis* of the structure grow to form a replicant structure.

* * * * *

SEQUENCE LISTING

<160> NUMBER OF SEQ ID NOS: 55

<210> SEQ ID NO 1
<211> LENGTH: 8
<212> TYPE: PRT
<213> ORGANISM: Bacillus subtilis

<400> SEQUENCE: 1

Gly Gly Gly Ser Gly Gly Gly Ser
1               5

<210> SEQ ID NO 2
<211> LENGTH: 10
<212> TYPE: PRT
<213> ORGANISM: Bacillus subtilis

<400> SEQUENCE: 2

Gly Gly Gly Gly Ser Gly Gly Gly Gly Ser
1               5                   10

<210> SEQ ID NO 3
<211> LENGTH: 33
<212> TYPE: DNA
<213> ORGANISM: Bacillus subtilis

<400> SEQUENCE: 3
ggggtcgaca tgtttcgatt gtttcacaat cag          33

<210> SEQ ID NO 4
<211> LENGTH: 43
<212> TYPE: DNA
<213> ORGANISM: Bacillus subtilis

<400> SEQUENCE: 4

-continued tcataccgta aatcctttct gattaagtag acatggtgct gtc 43

<210> SEQ ID NO 5
<211> LENGTH: 43
<212> TYPE: DNA
<213> ORGANISM: Bacillus subtilis

<400> SEQUENCE: 5
gacagcacca tgtctactta atcagaaagg atttacggta tga 43

<210> SEQ ID NO 6
<211> LENGTH: 30
<212> TYPE: DNA
<213> ORGANISM: Bacillus subtilis

<400> SEQUENCE: 6
gcgagatctg cgtttttttc aagcaaacag 30

<210> SEQ ID NO 7
<211> LENGTH: 29
<212> TYPE: DNA
<213> ORGANISM: Bacillus subtilis

<400> SEQUENCE: 7
aaaggatccg caatcctcgg actggcggg 29

<210> SEQ ID NO 8
<211> LENGTH: 46
<212> TYPE: DNA
<213> ORGANISM: Bacillus subtilis

<400> SEQUENCE: 8
gagaatcaaa ataaaccttc cgcgtattca tagccttcag ccttcc 46

<210> SEQ ID NO 9
<211> LENGTH: 46
<212> TYPE: DNA
<213> ORGANISM: Bacillus subtilis

<400> SEQUENCE: 9
ggaaggctga aggctatgaa tacgcggaag gtttattttg attctc 46

<210> SEQ ID NO 10
<211> LENGTH: 29
<212> TYPE: DNA
<213> ORGANISM: Bacillus subtilis

<400> SEQUENCE: 10
aaagtcgact tccgctgcga tgtgcccat 29

<210> SEQ ID NO 11
<211> LENGTH: 39
<212> TYPE: DNA
<213> ORGANISM: Bacillus subtilis

<400> SEQUENCE: 11
gggggatcca tgggtatgaa aaagaaattg agtttagga 39

<210> SEQ ID NO 12
<211> LENGTH: 39
<212> TYPE: DNA
<213> ORGANISM: Bacillus subtilis

<400> SEQUENCE: 12
gggcccgggt taatttttat cctcgctatg cgctttttc 39

<210> SEQ ID NO 13
<211> LENGTH: 39
<212> TYPE: DNA
<213> ORGANISM: Bacillus subtilis

<400> SEQUENCE: 13
gggcccgggt tagtggtggt ggtggtggtg atttttatc 39

<210> SEQ ID NO 14
<211> LENGTH: 93
<212> TYPE: DNA
<213> ORGANISM: Bacillus subtilis

<400> SEQUENCE: 14
gggcccgggt tatttggtgg gtttatatgc atcgaccata acgatgtgcg cggagccccc 60
gccggagccc ccgccatttt tatcctcgct atg 93

<210> SEQ ID NO 15
<211> LENGTH: 85
<212> TYPE: DNA
<213> ORGANISM: Bacillus subtilis

<400> SEQUENCE: 15
tctttattat aagaattgtg gaattgtgag cggataacaa ttcccaatta aaggaggaag 60
atgggtatga aaaagaaatt gagtt 85

<210> SEQ ID NO 16
<211> LENGTH: 87
<212> TYPE: DNA
<213> ORGANISM: Bacillus subtilis

<400> SEQUENCE: 16
ttcgggccat agtaatccgc ggatcctgag cctcctcctc ctgatcctcc gccgccgccg 60
gcatttttat cctcgctatg cgctttt 87

<210> SEQ ID NO 17
<211> LENGTH: 87
<212> TYPE: DNA
<213> ORGANISM: Bacillus subtilis

<400> SEQUENCE: 17
aaaagcgcat agcgaggata aaaatgccgg cggcggcgga ggatcaggag gaggaggctc 60
aggatccgcg gattactatg gcccgaa 87

<210> SEQ ID NO 18
<211> LENGTH: 112
<212> TYPE: DNA
<213> ORGANISM: Bacillus subtilis

<400> SEQUENCE: 18
tgaaaaaagc ccgctcatta ggcgggctgc cccggggacg tcgactctag aggatcttat 60
ggccaatgat gatggtgatg atggtgacta gtccagtatt tgccgcgtct gc 112

<210> SEQ ID NO 19
<211> LENGTH: 89
<212> TYPE: DNA
<213> ORGANISM: Bacillus subtilis

<400> SEQUENCE: 19
cgcccttata ctcttcgctg ctggatcctg agcctcctcc tcctgatcct ccgccgccgc 60
cggcattttt atcctcgcta tgcgctttt 89

<210> SEQ ID NO 20
<211> LENGTH: 89
<212> TYPE: DNA
<213> ORGANISM: Bacillus subtilis

<400> SEQUENCE: 20
aaaagcgcat agcgaggata aaaatgccgg cggcggcgga ggatcaggag gaggaggctc 60
aggatccagc agcgaagagt ataagggcg 89

<210> SEQ ID NO 21
<211> LENGTH: 114
<212> TYPE: DNA
<213> ORGANISM: Bacillus subtilis

<400> SEQUENCE: 21
tgaaaaaagc ccgctcatta ggcgggctgc cccggggacg tcgactctag aggatcttat 60
ggccaatgat gatggtgatg atggtgacta gtgctgctgc cgccgtaata ctta 114

<210> SEQ ID NO 22
<211> LENGTH: 86
<212> TYPE: DNA
<213> ORGANISM: Bacillus subtilis

<400> SEQUENCE: 22
tccaaattgt gccgccgctg ccgccgccgc ctgatcctcc gccgccattt ttatcctcgc 60
tatgcgcttt ttcattttct ttcacg 86

<210> SEQ ID NO 23
<211> LENGTH: 86
<212> TYPE: DNA
<213> ORGANISM: Bacillus subtilis

<400> SEQUENCE: 23
cgtgaaagaa aatgaaaaag cgcatagcga ggataaaaat ggcggcggag gatcaggcgg 60
cggcggcagc ggcggcacaa tttgga 86

<210> SEQ ID NO 24
<211> LENGTH: 90
<212> TYPE: DNA
<213> ORGANISM: Bacillus subtilis

<400> SEQUENCE: 24
cgctcattag gcgggctgcc ccggggacgt cgactctaga ggatcttaat gatgatggtg 60
atgatggtgt gccagcgcat cgcgcagttc 90

<210> SEQ ID NO 25
<211> LENGTH: 87
<212> TYPE: DNA
<213> ORGANISM: Bacillus subtilis

<400> SEQUENCE: 25
gtgagcaagg gcgaggagga ggatcctgag cctcctcctc ctgatcctcc gccgccgccg 60
gcatttttat cctcgctatg cgctttt 87

<210> SEQ ID NO 26
<211> LENGTH: 87
<212> TYPE: DNA
<213> ORGANISM: Bacillus subtilis

<400> SEQUENCE: 26
aaaagcgcat agcgaggata aaaatgccgg cggcggcgga ggatcaggag gaggaggctc 60
aggatccgtg agcaagggcg aggagga 87

<210> SEQ ID NO 27
<211> LENGTH: 107
<212> TYPE: DNA
<213> ORGANISM: Bacillus subtilis

<400> SEQUENCE: 27
tgaaaaaagc ccgctcatta ggcgggctgc cccggggacg tcgactctag aggatcttaa 60
tgatgatggt gatgatggtg actagtaccc gccttgtaca gctcgtc 107

<210> SEQ ID NO 28
<211> LENGTH: 47
<212> TYPE: DNA
<213> ORGANISM: Bacillus subtilis

<400> SEQUENCE: 28
ccgcctgatc ctccgccgcc gccggcattt ttatcctcgc tatgcgc 47

<210> SEQ ID NO 29
<211> LENGTH: 23
<212> TYPE: DNA
<213> ORGANISM: Bacillus subtilis

<400> SEQUENCE: 29
cgtgaaagaa aatgaaaaag cgc 23

<210> SEQ ID NO 30
<211> LENGTH: 22
<212> TYPE: DNA
<213> ORGANISM: Bacillus subtilis

<400> SEQUENCE: 30
tgaaaaaagc ccgctcatta gg 22

<210> SEQ ID NO 31
<211> LENGTH: 24
<212> TYPE: DNA
<213> ORGANISM: Bacillus subtilis

<400> SEQUENCE: 31
tcaggatcct ctatcggtac cggt 24

<210> SEQ ID NO 32
<211> LENGTH: 43
<212> TYPE: DNA
<213> ORGANISM: Bacillus subtilis

<400> SEQUENCE: 32
gactctagag gatcttaact agttgacgcc cgcaaggtcg gtg 43

<210> SEQ ID NO 33
<211> LENGTH: 783
<212> TYPE: DNA
<213> ORGANISM: Bacillus subtilis -continued

<400> SEQUENCE: 33
atgggtatga aaaagaaatt gagtttagga gttgcttctg cagcactagg attagcttta 60
gttggaggag gaacatgggc agcatttaac gacattaaat caaaggatgc tacttttgca 120
tcaggtacgc ttgatttatc tgctaaagag aattcagcga gtgtgaactt atcaaatcta 180
aagccgggag ataagttgac aaaggatttc caatttgaaa ataacggatc acttgcgatc 240
aaagaagttc taatggcgct taattatgga gattttaaag caaacggcgg cagcaataca 300
tctccagaag atttcctcag ccagtttgaa gtgacattgt tgacagttgg aaaagagggc 360
ggcaatggct acccgaaaaa cattatttta gatgatgcga accttaaaga cttgtatttg 420
atgtctgcta aaaatgatgc agcggctgct gaaaaaatca aaaaacaaat tgaccctaaa 480
ttcttaaatg caagcggtaa agtcaatgta gcaacaattg atggtaaaac cgctcctgaa 540
tatgatggtg ttccaaaaac accaactgac ttcgatcagg ttcaaatgga aatccaattc 600
aaggatgata aaacaaaaga tgaaaaaggg cttatggttc aaaataaata tcaaggcaac 660
tccattaagc ttcaattctc attcgaagct acacagtgga acggcttgac aatcaaaaag 720
gaccatactg ataaagatgg ttacgtgaaa gaaaatgaaa aagcgcatag cgaggataaa 780
aat 783

<210> SEQ ID NO 34
<211> LENGTH: 18
<212> TYPE: DNA
<213> ORGANISM: Bacillus subtilis

<400> SEQUENCE: 34
caccaccacc accaccac 18

<210> SEQ ID NO 35
<211> LENGTH: 39
<212> TYPE: DNA
<213> ORGANISM: Bacillus subtilis

<400> SEQUENCE: 35
gcgcacatcg ttatggtcga tgcatataaa cccaccaaa 39

<210> SEQ ID NO 36
<211> LENGTH: 1170
<212> TYPE: DNA
<213> ORGANISM: Bacillus subtilis

<400> SEQUENCE: 36
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccaa actgagcaaa gaccccaacg agaagcgcga tcacatggtc 660

-continued ctgctggagt tcgtgaccgc cgccgggatc actctcggca tggacgagct gtacaaggcg 720
ggtggcggtg gtggtagcgg tggtggcggt agctcgtact accatcacca tcaccatcac 780
gattacgaca tcccaacgac cgaaaacctg tattttcagg gcgccatggt aaccacctta 840
tcaggtttat caggtgagca aggtccgtcc ggtgatatga caactgaaga agatagtgct 900
acccatatta aattctcaaa acgtgatgag gacggccgtg agttagctgg tgcaactatg 960
gagttgcgtg attcatctgg taaaactatt agtacatgga tttcagatgg acatgtgaag 1020
gatttctacc tgtatccagg aaaatataca tttgtcgaaa ccgcagcacc agacggttat 1080
gaggtagcaa ctgctattac ctttacagtt aatgagcaag gtcaggttac tgtaaatggc 1140
gaagcaacta aaggtgacgc tcatacttaa 1170

<210> SEQ ID NO 37
<211> LENGTH: 177
<212> TYPE: DNA
<213> ORGANISM: Bacillus subtilis

<400> SEQUENCE: 37
ggcggcacaa tttggacagg caaaggcctt ggcctgggcc tgggacttgg acttggcgca 60
tggggcccga ttattctggg cgttgtgggc gcaggcgcag tgtatgcgta catgaaaagc 120
cgcgacatcg aatcagcgca tagcgacgaa gaagtggaac tgcgcgatgc gctggca 177

<210> SEQ ID NO 38
<211> LENGTH: 144
<212> TYPE: DNA
<213> ORGANISM: Bacillus subtilis

<400> SEQUENCE: 38
gcggattact atggcccgaa ttatggaccg ccgcgccgct atggaggcgg caattacaac 60
cgctataacc gctatggccg ccgctatggc ggctataagg gctggaataa cggctggaat 120
cgcggcagac gcggcaaata ctgg 144

<210> SEQ ID NO 39
<211> LENGTH: 222
<212> TYPE: DNA
<213> ORGANISM: Bacillus subtilis

<400> SEQUENCE: 39
agcagcgaag agtataaggg cggctattat cctggtaatg cgtatcacta ccattcaggc 60
ggcagctatc atggctcagg ctatcatggc ggctataagg gcaaatacta cggcaaggcg 120
aaaaaatatt attataaata taaaaatagc ggcaagtata aatatctgaa aaaagcgcgc 180
aaataccatc gcaagggcta taagtattac ggcggcagca gc 222

<210> SEQ ID NO 40
<211> LENGTH: 714
<212> TYPE: DNA
<213> ORGANISM: Bacillus subtilis

<400> SEQUENCE: 40
atggtgagca agggcgagga ggataacatg gccatcatca aggagttcat gcgcttcaag 60
gtgcacatgg agggctccgt gaacggccac gagttcgaga tcgagggcga gggcgagggc 120
cgcccctacg agggcaccca gaccgccaag ctgaaggtga ccaagggtgg cccccctgccc 180 ttcgcctggg acatcctgtc ccctcagttc atgtacggct ccaaggccta cgtgaagcac 240

-continued cccgccgaca tccccgacta cttgaagctg tccttccccg agggcttcaa gtgggagcgc 300
gtgatgaact tcgaggacgg cggcgtggtg accgtgaccc aggactcctc cctgcaggac 360
ggcgagttca tctacaaggt gaagctgcgc ggcaccaact tcccctccga cggccccgta 420
atgcagaaga agacgatggg ctgggaggcc tcctccgagc ggatgtaccc cgaggacggc 480
gccctgaagg gcgagatcaa gcagaggctg aagctgaagg acggcggcca ctacgacgct 540
gaggtcaaga ccacctacaa ggccaagaag cccgtgcagc tgcccggcgc ctacaacgtc 600
aacatcaagt tggacatcac ctcccacaac gaggactaca ccatcgtgga acagtacgaa 660
cgcgccgagg gccgccactc caccggcggc atggacgagc tgtacaaggc gggt 714

<210> SEQ ID NO 41
<211> LENGTH: 1011
<212> TYPE: DNA
<213> ORGANISM: Bacillus subtilis

<400> SEQUENCE: 41
atgtcaattg gcacgggcga tcgcatcaac acagtgagag gcccgatcac aattagcgaa 60
gcgggcttta cactgacgca tgagcatatc tgcggcagct cagcgggctt tcttcgcgca 120
tggccggaat tttttggcag ccgcaaagcg ctggcagaaa aagcggtgag aggcctgaga 180
agagcgagag cagcgggcgt tcgcacgatt gtggatgtga gcacgtttga catcggcaga 240
gatgtgagcc tgctggcgga agttagccgc gcagcagatg tgcatatcgt ggcagcgacg 300
ggactgtggt ttgatccgcc tcttagcatg cgccttcgca gcgtggagga actgacgcag 360
tttttcctgc gcgaaatcca gtacggcatc gaagatacgg gcattagagc gggcatcatc 420
aaagtggcga caacgggaaa ggcaacaccg tttcaggagc tggttctgaa agcagcagca 480
agagcatcac tggcgacagg cgtgccggtt acgacacata cagcagcgtc acagcgcgat 540
ggcgaacaac aggcggcgat cttcgaatca gaaggcctgt caccttcacg cgtgtgtatc 600
ggccatagcg atgatacgga cgatctgagc tacctgacag cactggcggc acgcggctat 660
ctgattggcc tggaccatat cccgcactca gcaatcggcc tggaagataa tgcgagcgca 720
agcgcgctgc tgggcattag aagctggcag acgagagcgc ttctgatcaa ggcgctgatc 780
gatcagggct acatgaagca gattctggtg agcaacgact ggctgtttgg cttcagcagc 840
tatgtgacga acattatgga cgtgatggat cgcgtgaatc cggatggcat ggcatttatc 900
ccgctgagag tgatcccgtt tcttcgcgaa aaaggcgtgc cgcaggaaac actggcaggc 960
atcacggtga caaatccggc gagatttctg agcccgacac tgagagcgag c 1011

<210> SEQ ID NO 42
<211> LENGTH: 711
<212> TYPE: DNA
<213> ORGANISM: Bacillus subtilis

<400> SEQUENCE: 42
atggtgagca aaggcgagga gacaatcatg tccgtgatca agcccgacat gaagatcaaa 60
ctgaggatgg agggcaacgt gaacggccac gccttcgtga tcgagggcga aggaagcggc 120
aagcccttcg agggcatcca gaccatcgat ctggaggtca aggagggcgc tcccctccct 180
ttcgcctatg acatcctgac caccgccttc cactacggca atagggtgtt caccaagtat 240
cccaggaaga tccccgacta cttcaagcag agcttccctg agggctacag ctgggagagg 300
agcatgacat acgaggacgg cggcatctgc aacgccacca acgacatcac aatggaggag 360
gacagcttca tcaacaagat ccacttcaaa ggcacaaact tcccccccaa tggccccgtg 420
atgcagaaga ggaccgtggg ctgggaggtg agcaccgaga agatgtacgt gagggacggc 480
gtcctgaagg gcgacgtgaa gatgaagctc ctgctcaagg gcggcagcca ctacaggtgc 540
gactttagga ccacctataa ggtgaagcag aaggctgtga agctgcccaa ggcccacttc 600
gtcgaccata ggatcgagat cctgtcccac gacaaggact acaacaaggt caagctgtac 660
gagcacgccg tcgctaggaa cagcaccgac agcatggacg aactctataa g 711

<210> SEQ ID NO 43
<211> LENGTH: 870
<212> TYPE: DNA
<213> ORGANISM: Bacillus subtilis

<400> SEQUENCE: 43
atgaactttc cgagagcgag cagactgatg caagcggcag tgcttggagg ccttatggcg 60
gtttcagcgg cggcaacagc gcagacaaat ccgtatgcga gaggaccgaa tccgacggca 120
gcgtcacttg aagcgagcgc tggtccgttt acagttcgca gcttcacagt gagcagaccg 180
tctggttatg gcgctggtac ggtgtattat ccgacaaatg ctggtggcac ggttggagca 240
attgcgattg tgccgggcta cacagcgcgc caaagcagca ttaaatggtg gggccctaga 300
ctggcaagcc acggctttgt ggtgatcacg attgacacga acagcacact ggaccagccg 360
agctcaagaa gcagccaaca aatggcggca ctgcgccaag ttgcatcttt aaatggcacg 420
tcaagcagcc cgatctatgg caaagtggat acggcgcgca tgggagtgat gggatggtca 480
atgggaggcg gaggctcact gatcagcgcg gcaaataacc cgtctttaaa agcggcagca 540
ccgcaagcgc cttgggatag cagcacaaac ttcagcagcg ttacggtgcc gacactgatc 600
tttgcgtgcg agaacgatag catcgcgccg gttaattcta gcgcgctgcc gatttacgac 660
agcatgtcac gcaacgcgaa acaattttta gagatcaacg gcggcagcca ttcatgcgcg 720
aacagcggca atagcaacca agctctgatc ggcaaaaaag gagtggcatg gatgaagcgc 780
ttcatggata acgacacgcg ctacagcaca ttcgcgtgcg aaaacccgaa cagcacgaga 840
gtgagcgatt ttcgcacggc gaattgctca 870

<210> SEQ ID NO 44
<211> LENGTH: 1809
<212> TYPE: DNA
<213> ORGANISM: Bacillus subtilis

<400> SEQUENCE: 44
atgcagacaa cagtgacgac aatgctgctg gcatcagtgg cgcttgcagc atgtgctggt 60
ggaggctcaa caccgctgcc gcttccgcag caacaaccgc ctcaacaaga acctccgccg 120
ccgcccgttc cgcttgcgtc aagagcagcg tgcgaagcgc ttaaagatgg caatggcgac 180
atggtgtggc cgaatgcagc aacagtggtt gaagtggcgg catggagaga tgcagcaccc 240
gctacagcaa gcgcagcggc acttccggaa cattgcgaag tgtctggtgc gattgcgaaa 300
cgcacgggaa ttgatggcta cccgtacgag atcaaatttc gccttcgcat gccggcagag 360
tggaatggcc gctttttcat ggaaggcgga agcggaacga atggctcact ttcagcggca 420
actggtagca tcggcggagg ccagattgca agcgcactga gccgcaattt tgcgacaatc 480
gcaacggacg gcggccatga taatgcggtg aacgataacc cggacgcact gggcacagtg 540
gcattcggcc ttgatccgca agctagactg gacatgggct ataacagcta cgatcaagtt 600
acgcaagcgg gcaaagcagc ggtggcgaga ttttacggca gagcggcgga caaaagctac 660

```
tttatcggat gctcagaggg cggcagagaa ggcatgatgc tgtcacagcg ctttccgtca    720

cactatgatg gcatcgttgc gggcgcaccg ggatatcagc tgccgaaagc gggcatttct    780

ggtgcatgga cgacacaaag ccttgcgccc gctgctgttg gccttgacgc gcaaggtgtt    840

ccgctgatca acaagagctt tagcgacgcg gatcttcacc ttctgagcca agcgattctg    900

ggaacatgcg atgcgctgga tggtttagcg gatggcattg ttgacaacta cagagcgtgc    960

caagctgcgt ttgacccggc gacagcagca aacccggcaa atggccaagc tttacaatgc   1020

gtgggcgcaa aaacagcgga ttgtttaagc ccggttcaag ttacggcgat caagcgcgca   1080

atggctggtc cggtgaacag cgctggtaca ccgctgtata acagatgggc atgggatgct   1140

ggtatgagcg gtttaagcgg cacaacgtac aaccaaggtt ggcgctcatg gtggcttggc   1200

agcttcaatt caagcgcgaa caacgcgcag agagttagcg gcttttcagc gagaagctgg   1260

ctggtggatt tcgcgacacc gccggaaccg atgccgatga cacaagttgc ggcaagaatg   1320

atgaagttcg acttcgacat cgatccgctg aaaatctggg cgacaagcgg ccagtttacg   1380

cagtcaagca tggattggca cggagcgaca agcacagatc tggcggcatt tcgcgatcgc   1440

ggcggcaaga tgattctgta ccatggaatg agcgacgcgg cgtttagcgc gctggatacg   1500

gcggactact atgagcgcct tggagcagca atgccgggag cagctggttt tgcacgcctt   1560

ttccttgtgc cgggcatgaa ccattgcagc ggcggaccgg gaacagatcg cttcgacatg   1620

cttacaccgc tggtggcatg ggttgaaaga ggcgaagcgc cggatcagat cagcgcatgg   1680

agcggcacac cgggctattt tggagtggca gcaagaacga gaccgctgtg tccgtatccg   1740

cagatcgcgc gctacaaagg aagcggcgat atcaacacag aagcgaattt tgcatgcgcg   1800

gcaccgcct                                                           1809


<210> SEQ ID NO 45
<211> LENGTH: 261
<212> TYPE: PRT
<213> ORGANISM: Bacillus subtilis

<400> SEQUENCE: 45

Met Gly Met Lys Lys Lys Leu Ser Leu Gly Val Ala Ser Ala Ala Leu
1               5                   10                  15

Gly Leu Ala Leu Val Gly Gly Gly Thr Trp Ala Ala Phe Asn Asp Ile
            20                  25                  30

Lys Ser Lys Asp Ala Thr Phe Ala Ser Gly Thr Leu Asp Leu Ser Ala
        35                  40                  45

Lys Glu Asn Ser Ala Ser Val Asn Leu Ser Asn Leu Lys Pro Gly Asp
    50                  55                  60

Lys Leu Thr Lys Asp Phe Gln Phe Glu Asn Asn Gly Ser Leu Ala Ile
65                  70                  75                  80

Lys Glu Val Leu Met Ala Leu Asn Tyr Gly Asp Phe Lys Ala Asn Gly
                85                  90                  95

Gly Ser Asn Thr Ser Pro Glu Asp Phe Leu Ser Gln Phe Glu Val Thr
            100                 105                 110

Leu Leu Thr Val Gly Lys Glu Gly Gly Asn Gly Tyr Pro Lys Asn Ile
        115                 120                 125

Ile Leu Asp Asp Ala Asn Leu Lys Asp Leu Tyr Leu Met Ser Ala Lys
    130                 135                 140

Asn Asp Ala Ala Ala Ala Glu Lys Ile Lys Lys Gln Ile Asp Pro Lys
145                 150                 155                 160

Phe Leu Asn Ala Ser Gly Lys Val Asn Val Ala Thr Ile Asp Gly Lys
```

```
                165                 170                 175

Thr Ala Pro Glu Tyr Asp Gly Val Pro Lys Thr Pro Thr Asp Phe Asp
            180                 185                 190

Gln Val Gln Met Glu Ile Gln Phe Lys Asp Asp Lys Thr Lys Asp Glu
        195                 200                 205

Lys Gly Leu Met Val Gln Asn Lys Tyr Gln Gly Asn Ser Ile Lys Leu
    210                 215                 220

Gln Phe Ser Phe Glu Ala Thr Gln Trp Asn Gly Leu Thr Ile Lys Lys
225                 230                 235                 240

Asp His Thr Asp Lys Asp Gly Tyr Val Lys Glu Asn Glu Lys Ala His
                245                 250                 255

Ser Glu Asp Lys Asn
            260


<210> SEQ ID NO 46
<211> LENGTH: 6
<212> TYPE: PRT
<213> ORGANISM: Bacillus subtilis

<400> SEQUENCE: 46

His His His His His His
1               5


<210> SEQ ID NO 47
<211> LENGTH: 13
<212> TYPE: PRT
<213> ORGANISM: Bacillus subtilis

<400> SEQUENCE: 47

Ala His Ile Val Met Val Asp Ala Tyr Lys Pro Thr Lys
1               5                   10


<210> SEQ ID NO 48
<211> LENGTH: 59
<212> TYPE: PRT
<213> ORGANISM: Bacillus subtilis

<400> SEQUENCE: 48

Gly Gly Thr Ile Trp Thr Gly Lys Gly Leu Gly Leu Gly Leu Gly Leu
1               5                   10                  15

Gly Leu Gly Ala Trp Gly Pro Ile Ile Leu Gly Val Val Gly Ala Gly
            20                  25                  30

Ala Val Tyr Ala Tyr Met Lys Ser Arg Asp Ile Glu Ser Ala His Ser
        35                  40                  45

Asp Glu Glu Val Glu Leu Arg Asp Ala Leu Ala
    50                  55


<210> SEQ ID NO 49
<211> LENGTH: 48
<212> TYPE: PRT
<213> ORGANISM: Bacillus subtilis

<400> SEQUENCE: 49

Ala Asp Tyr Tyr Gly Pro Asn Tyr Gly Pro Pro Arg Arg Tyr Gly Gly
1               5                   10                  15

Gly Asn Tyr Asn Arg Tyr Asn Arg Tyr Gly Arg Arg Tyr Gly Gly Tyr
            20                  25                  30

Lys Gly Trp Asn Asn Gly Trp Asn Arg Gly Arg Arg Gly Lys Tyr Trp
        35                  40                  45
```

<210> SEQ ID NO 50
<211> LENGTH: 74
<212> TYPE: PRT
<213> ORGANISM: Bacillus subtilis

<400> SEQUENCE: 50

```
Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Tyr Tyr Gly Gly Ser Ser
65                  70
```

<210> SEQ ID NO 51
<211> LENGTH: 237
<212> TYPE: PRT
<213> ORGANISM: Bacillus subtilis

<400> SEQUENCE: 51

```
Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys Ala Gly
225                 230                 235
```

<210> SEQ ID NO 52
<211> LENGTH: 337

<212> TYPE: PRT
<213> ORGANISM: Bacillus subtilis

<400> SEQUENCE: 52

```
Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro His Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser
```

<210> SEQ ID NO 53
<211> LENGTH: 237
<212> TYPE: PRT
<213> ORGANISM: Bacillus subtilis

<400> SEQUENCE: 53

```
Met Val Ser Lys Gly Glu Glu Thr Ile Met Ser Val Ile Lys Pro Asp
```

-continued

```
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro Phe Ala Tyr Asp
    50                  55                  60

Ile Leu Thr Thr Ala Phe His Tyr Gly Asn Arg Val Phe Thr Lys Tyr
65                  70                  75                  80

Pro Arg Lys Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Asn Ala
            100                 105                 110

Thr Asn Asp Ile Thr Met Glu Glu Asp Ser Phe Ile Asn Lys Ile His
        115                 120                 125

Phe Lys Gly Thr Asn Phe Pro Pro Asn Gly Pro Val Met Gln Lys Arg
    130                 135                 140

Thr Val Gly Trp Glu Val Ser Thr Glu Lys Met Tyr Val Arg Asp Gly
145                 150                 155                 160

Val Leu Lys Gly Asp Val Lys Met Lys Leu Leu Leu Lys Gly Gly Ser
                165                 170                 175

His Tyr Arg Cys Asp Phe Arg Thr Thr Tyr Lys Val Lys Gln Lys Ala
            180                 185                 190

Val Lys Leu Pro Lys Ala His Phe Val Asp His Arg Ile Glu Ile Leu
        195                 200                 205

Ser His Asp Lys Asp Tyr Asn Lys Val Lys Leu Tyr Glu His Ala Val
    210                 215                 220

Ala Arg Asn Ser Thr Asp Ser Met Asp Glu Leu Tyr Lys
225                 230                 235


<210> SEQ ID NO 54
<211> LENGTH: 290
<212> TYPE: PRT
<213> ORGANISM: Bacillus subtilis

<400> SEQUENCE: 54

Met Asn Phe Pro Arg Ala Ser Arg Leu Met Gln Ala Ala Val Leu Gly
1               5                   10                  15

Gly Leu Met Ala Val Ser Ala Ala Ala Thr Ala Gln Thr Asn Pro Tyr
            20                  25                  30

Ala Arg Gly Pro Asn Pro Thr Ala Ala Ser Leu Glu Ala Ser Ala Gly
        35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
    130                 135                 140
```

```
Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
    210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Arg Val Ser Asp Phe Arg Thr Ala Asn
        275                 280                 285

Cys Ser
    290


<210> SEQ ID NO 55
<211> LENGTH: 603
<212> TYPE: PRT
<213> ORGANISM: Bacillus subtilis

<400> SEQUENCE: 55

Met Gln Thr Thr Val Thr Thr Met Leu Leu Ala Ser Val Ala Leu Ala
1               5                   10                  15

Ala Cys Ala Gly Gly Gly Ser Thr Pro Leu Pro Leu Pro Gln Gln Gln
            20                  25                  30

Pro Pro Gln Gln Glu Pro Pro Pro Pro Pro Val Pro Leu Ala Ser Arg
        35                  40                  45

Ala Ala Cys Glu Ala Leu Lys Asp Gly Asn Gly Asp Met Val Trp Pro
    50                  55                  60

Asn Ala Ala Thr Val Val Glu Val Ala Ala Trp Arg Asp Ala Ala Pro
65                  70                  75                  80

Ala Thr Ala Ser Ala Ala Ala Leu Pro Glu His Cys Glu Val Ser Gly
                85                  90                  95

Ala Ile Ala Lys Arg Thr Gly Ile Asp Gly Tyr Pro Tyr Glu Ile Lys
            100                 105                 110

Phe Arg Leu Arg Met Pro Ala Glu Trp Asn Gly Arg Phe Phe Met Glu
        115                 120                 125

Gly Gly Ser Gly Thr Asn Gly Ser Leu Ser Ala Ala Thr Gly Ser Ile
    130                 135                 140

Gly Gly Gly Gln Ile Ala Ser Ala Leu Ser Arg Asn Phe Ala Thr Ile
145                 150                 155                 160

Ala Thr Asp Gly Gly His Asp Asn Ala Val Asn Asp Asn Pro Asp Ala
                165                 170                 175

Leu Gly Thr Val Ala Phe Gly Leu Asp Pro Gln Ala Arg Leu Asp Met
            180                 185                 190

Gly Tyr Asn Ser Tyr Asp Gln Val Thr Gln Ala Gly Lys Ala Ala Val
        195                 200                 205

Ala Arg Phe Tyr Gly Arg Ala Ala Asp Lys Ser Tyr Phe Ile Gly Cys
    210                 215                 220
```

-continued

```
Ser Glu Gly Gly Arg Glu Gly Met Met Leu Ser Gln Arg Phe Pro Ser
225                 230                 235                 240

His Tyr Asp Gly Ile Val Ala Gly Ala Pro Gly Tyr Gln Leu Pro Lys
                245                 250                 255

Ala Gly Ile Ser Gly Ala Trp Thr Thr Gln Ser Leu Ala Pro Ala Ala
            260                 265                 270

Val Gly Leu Asp Ala Gln Gly Val Pro Leu Ile Asn Lys Ser Phe Ser
        275                 280                 285

Asp Ala Asp Leu His Leu Leu Ser Gln Ala Ile Leu Gly Thr Cys Asp
    290                 295                 300

Ala Leu Asp Gly Leu Ala Asp Gly Ile Val Asp Asn Tyr Arg Ala Cys
305                 310                 315                 320

Gln Ala Ala Phe Asp Pro Ala Thr Ala Ala Asn Pro Ala Asn Gly Gln
                325                 330                 335

Ala Leu Gln Cys Val Gly Ala Lys Thr Ala Asp Cys Leu Ser Pro Val
            340                 345                 350

Gln Val Thr Ala Ile Lys Arg Ala Met Ala Gly Pro Val Asn Ser Ala
        355                 360                 365

Gly Thr Pro Leu Tyr Asn Arg Trp Ala Trp Asp Ala Gly Met Ser Gly
    370                 375                 380

Leu Ser Gly Thr Thr Tyr Asn Gln Gly Trp Arg Ser Trp Trp Leu Gly
385                 390                 395                 400

Ser Phe Asn Ser Ser Ala Asn Asn Ala Gln Arg Val Ser Gly Phe Ser
                405                 410                 415

Ala Arg Ser Trp Leu Val Asp Phe Ala Thr Pro Pro Glu Pro Met Pro
            420                 425                 430

Met Thr Gln Val Ala Ala Arg Met Met Lys Phe Asp Phe Asp Ile Asp
        435                 440                 445

Pro Leu Lys Ile Trp Ala Thr Ser Gly Gln Phe Thr Gln Ser Ser Met
    450                 455                 460

Asp Trp His Gly Ala Thr Ser Thr Asp Leu Ala Ala Phe Arg Asp Arg
465                 470                 475                 480

Gly Gly Lys Met Ile Leu Tyr His Gly Met Ser Asp Ala Ala Phe Ser
                485                 490                 495

Ala Leu Asp Thr Ala Asp Tyr Tyr Glu Arg Leu Gly Ala Ala Met Pro
            500                 505                 510

Gly Ala Ala Gly Phe Ala Arg Leu Phe Leu Val Pro Gly Met Asn His
        515                 520                 525

Cys Ser Gly Gly Pro Gly Thr Asp Arg Phe Asp Met Leu Thr Pro Leu
    530                 535                 540

Val Ala Trp Val Glu Arg Gly Glu Ala Pro Asp Gln Ile Ser Ala Trp
545                 550                 555                 560

Ser Gly Thr Pro Gly Tyr Phe Gly Val Ala Ala Arg Thr Arg Pro Leu
                565                 570                 575

Cys Pro Tyr Pro Gln Ile Ala Arg Tyr Lys Gly Ser Gly Asp Ile Asn
            580                 585                 590

Thr Glu Ala Asn Phe Ala Cys Ala Ala Pro Pro
        595                 600
```